United States Patent
Stadler et al.

(10) Patent No.: US 8,401,646 B2
(45) Date of Patent: Mar. 19, 2013

(54) METHOD AND APPARATUS TO DETERMINE THE RELATIVE ENERGY EXPENDITURE FOR A PLURALITY OF PACING VECTORS

(75) Inventors: Robert W. Stadler, Shoreview, MN (US); Wade M. Demmer, Coon Rapids, MN (US); Todd J. Sheldon, North Oaks, MN (US)

(73) Assignee: Medtronic, Inc., Minneapolis, MN (US)

( * ) Notice: Subject to any disclaimer, the term of this patent is extended or adjusted under 35 U.S.C. 154(b) by 47 days.

(21) Appl. No.: 13/194,100

(22) Filed: Jul. 29, 2011

(65) Prior Publication Data

US 2012/0101546 A1 Apr. 26, 2012

Related U.S. Application Data

(63) Continuation-in-part of application No. 12/909,057, filed on Oct. 21, 2010.

(51) Int. Cl.
*A61B 1/00* (2006.01)
(52) U.S. Cl. .......................................................... 607/28
(58) Field of Classification Search ...................... 607/28
See application file for complete search history.

(56) References Cited

U.S. PATENT DOCUMENTS

| | | | |
|---|---|---|---|
| 5,458,624 A * | 10/1995 | Renirie et al. ................. | 607/29 |
| 5,707,398 A | 1/1998 | Lu | |
| 5,814,088 A | 9/1998 | Paul | |
| 5,897,577 A | 4/1999 | Cinbis | |
| 6,016,448 A | 1/2000 | Busacker | |
| 6,185,460 B1 | 2/2001 | Thompson | |
| 6,317,633 B1 | 11/2001 | Jorgenson | |
| 6,820,019 B1 | 11/2004 | Kelly | |
| 6,901,293 B2 | 5/2005 | Rogers | |
| 7,107,093 B2 | 9/2006 | Burnes | |
| 7,123,963 B2 | 10/2006 | Sawchuk | |
| 7,123,964 B2 | 10/2006 | Betzold | |
| 7,142,923 B2 | 11/2006 | North | |
| 7,292,889 B2 | 11/2007 | Gordon | |
| 7,324,949 B2 | 1/2008 | Bristol | |
| 7,555,336 B2 | 6/2009 | Sheth | |
| 7,680,536 B2 | 3/2010 | Sathaye | |
| 7,697,977 B2 | 4/2010 | Yonce | |
| 7,787,948 B2 | 8/2010 | Ross | |
| 7,848,812 B2 * | 12/2010 | Crowley et al. ................. | 607/29 |
| 7,894,894 B2 | 2/2011 | Stadler | |
| 2002/0161328 A1 | 10/2002 | Rogers | |
| 2002/0177879 A1 | 11/2002 | Ding | |
| 2004/0098056 A1 | 5/2004 | Ding | |
| 2004/0102812 A1 | 5/2004 | Yonce | |
| 2008/0077189 A1 | 3/2008 | Ostroff | |
| 2008/0294218 A1 | 11/2008 | Savage | |
| 2009/0043351 A1 | 2/2009 | Sathaye | |
| 2009/0156957 A1 | 6/2009 | Linder | |
| 2010/0137993 A1 | 6/2010 | Parrott | |
| 2011/0022110 A1 | 1/2011 | Min | |
| 2011/0022112 A1 | 1/2011 | Min | |

* cited by examiner

*Primary Examiner* — George Manual
(74) *Attorney, Agent, or Firm* — Carol F. Barry

(57) ABSTRACT

A medical device system determines and displays relative energy expenditure information for programmable parameter values. The system establishes a programmable parameter and multiple values of the parameter to be compared. A module performs a measurements for each of the multiple values and related to energy expenditure of a battery of an implantable medical device when operating according to each of the multiple parameter values. An energy expenditure for each of the values is computed using the measurements, and a graphical user interface is generated for displaying information corresponding to the computed energy expenditure for multiple parameter values.

25 Claims, 12 Drawing Sheets

LV Test Results

LV Pace Polarity: LV1 to LV2    LV Amplitude: 3.00 V    LV Pulse Width: 0.40 ms

| LV Pace Polarity | Absolute Longevity* | Amplitude Threshold | Pulse Width Threshold | Phrenic Nerve Stim Present? | Last Impedance |
|---|---|---|---|---|---|
| LV1 to RV coil | 10.2 Years | 0.4V @ 0.5ms | Not Tested | Not Tested | 567 ohms |
| LV2 to RV coil | 10.1 Years | 0.4V @ 0.5ms | Not Tested | Not Tested | 369 ohms |
| LV3 to RV coil | 10.0 Years | 0.6V @ 0.5ms | Not Tested | Not Tested | 399 ohms |
| LV4 to RV coil | 9.1 Years | 2.0V @ 0.5ms | Not Tested | Not Tested | 328 ohms |
| LV1 to LV2 | 10.2 Years | 0.6V @ 0.5ms | Not Tested | Not Tested | 885 ohms |
| LV1 to LV3 | 10.2 Years | 0.6V @ 0.5ms | Not Tested | Not Tested | 936 ohms |
| LV1 to LV4 | 10.2 Years | 0.5V @ 0.5ms | Not Tested | Not Tested | 853 ohms |
| LV2 to LV1 | 10.2 Years | 0.8V @ 0.5ms | Not Tested | Not Tested | 828 ohms |
| LV2 to LV3 | 10.1 Years | 0.7V @ 0.5ms | Not Tested | Not Tested | 521 ohms |
| LV2 to LV4 | 10.2 Years | 0.7V @ 0.5ms | Not Tested | Not Tested | 635 ohms |
| LV3 to LV1 | 10.2 Years | 0.9V @ 0.5ms | Not Tested | Not Tested | 853 ohms |
| LV3 to LV2 | 10.0 Years | 0.7V @ 0.5ms | Not Tested | Not Tested | 500 ohms |
| LV3 to LV4 | 10.2 Years | 0.7V @ 0.5ms | Not Tested | Not Tested | 634 ohms |
| LV4 to LV1 | 9.7 Years | 1.3V @ 0.5ms | Not Tested | Not Tested | 745 ohms |
| LV4 to LV2 | 8.6 Years | 2.2V @ 0.5ms | Not Tested | Not Tested | 622 ohms |
| LV4 to LV3 | 8.6 Years | 2.2V @ 0.5ms | Not Tested | Not Tested | 631 ohms |

[Edit] [Undo Printing] [Print...] [PROGRAM] [Close]

*Absolute longevity calculation includes a 1.5V LV safety margin.

FIG. 12

METHOD AND APPARATUS TO DETERMINE THE RELATIVE ENERGY EXPENDITURE FOR A PLURALITY OF PACING VECTORS

CROSS-REFERENCE TO RELATED APPLICATION

This disclosure is a continuation-in-part of U.S. patent application Ser. No. 12/909,057, filed on Oct. 21, 2010, and entitled "CAPTURE THRESHOLD MEASUREMENT FOR SELECTION OF PACING VECTOR", hereby incorporated herein by reference in its entirety.

FIELD OF THE DISCLOSURE

The disclosure relates generally to medical devices for delivering electrical stimulation and, in particular, to an apparatus and method for determining the relative energy expenditure for multiple pacing vectors.

BACKGROUND

As multi-polar cardiac pacing leads become commercially available, multiple bipolar pacing electrode vectors are possible. A clinician selecting which pacing electrode vector to use for pacing a patient's heart may consider, among other things, the pacing capture threshold, the hemodynamic benefit, and the avoidance of extra-cardiac stimulation. When selecting a pacing electrode vector, it is generally desired to avoid selecting an electrode pair that results in relatively high energy expenditure, e.g. due to high pacing capture threshold, in order to avoid early depletion of the pacemaker battery. A need remains for an apparatus and method for providing a clinician with useful information for selecting an optimal pacing electrode vector.

BRIEF DESCRIPTION OF THE DRAWINGS

FIG. 12 shows a GUI including actual battery longevity values rather than relative differences according to an alternative embodiment.

DETAILED DESCRIPTION

Figure 1:
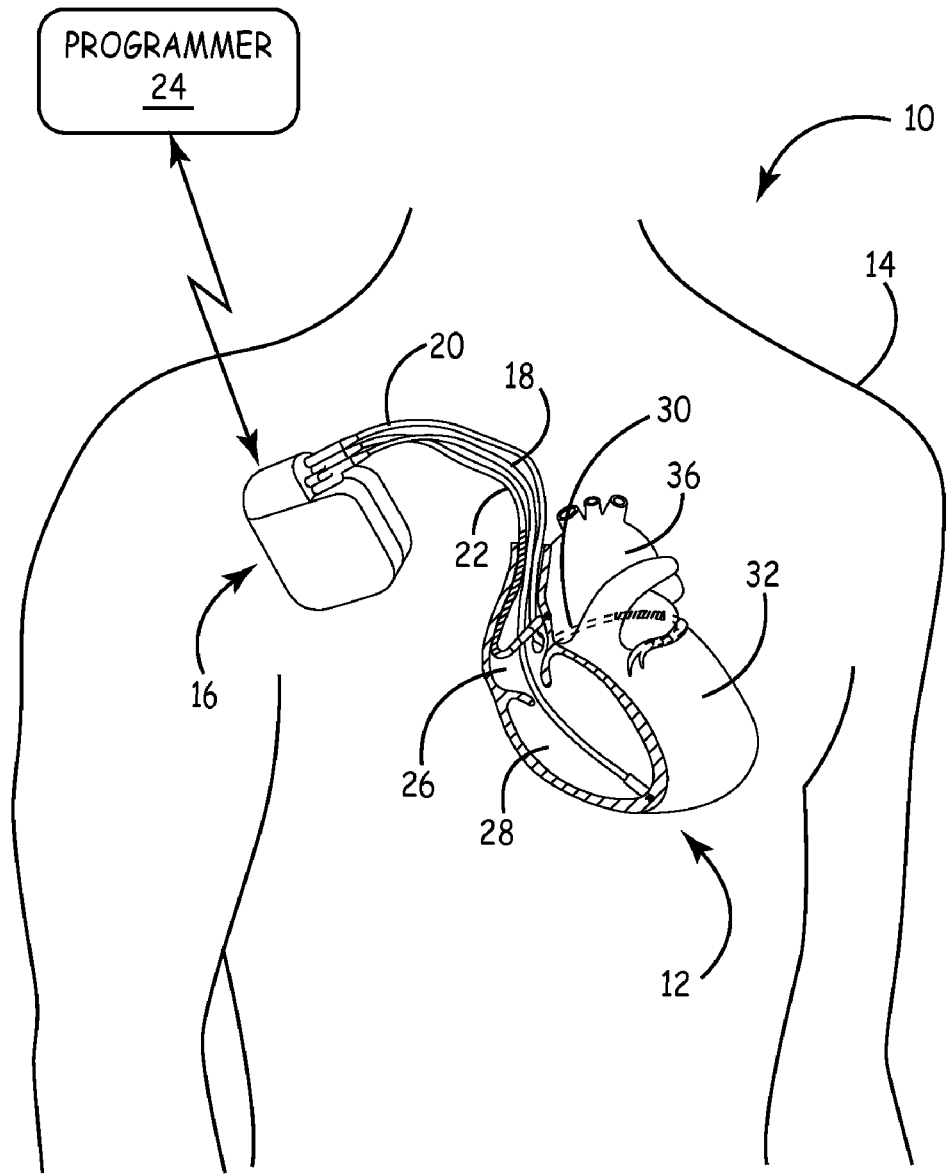
FIG. 1 is a conceptual diagram illustrating an example system that may be used to monitor and/or provide therapy to the heart of a patient.

In the following description, references are made to illustrative embodiments. It is understood that other embodiments may be utilized without departing from the scope of the disclosure. As used herein, the term "module" refers to an application specific integrated circuit (ASIC), an electronic circuit, a processor (shared, dedicated, or group) and memory that executes one or more software or firmware programs, a combinational logic circuit, or other suitable components that provide the described functionality.

This disclosure describes techniques for determining and displaying a comparative analysis of relative energy expenditure of programmable parameters to facilitate selection of operating parameters of an implantable medical device. In illustrative examples described herein, the relative energy expenditure of different pacing vectors used to pace the heart is determined and displayed to facilitate pacing vector selection. Energy expenditure, as referred to herein, may be expressed in actual or relative estimated energy usage or actual or relative predicted battery longevity when the IMD operates using a particular parameter selection.

Measuring pacing capture thresholds and lead impedance for multiple pacing vectors then computing and comparing the relative energy expenditure of these pacing vectors will facilitate selection of one of the vectors based on expected device longevity and desired therapeutic effect. The expected battery life of the implantable device using a particular pacing vector can be computed knowing the pacing capture threshold and associated lead impedance. Relative differences in the energy expenditure between different candidate pacing vectors are computed and displayed thereby allowing a clinician to select particular vectors for the implantable medical device (IMD) that will deliver sufficient energy to pace the heart without unnecessarily depleting the battery.

Although the following description refers to examples in which multiple LV pacing vectors are compared, it is to be understood that the disclosure is broadly applicable to any chambers of the heart being stimulated, and to any type of stimulation. Although described herein primarily with reference to examples in which voltage amplitude is adjusted during a capture threshold test for a vector to identify a voltage amplitude at which capture or loss of capture (LOC) occurs, the techniques are applicable to examples in which any one or more parameters that affect the energy of the pacing stimulus are adjusted, including pulse width, pulse shape, pulse amplitude, and safety pacing margin.

Furthermore, the techniques for computing relative energy expenditures and displaying comparative results to facilitate IMD programming is not limited to programmable parameters relating only to pacing vector selection. Rather, the techniques described herein may be broadly applied to a variety of programmable parameters and may be applied to any combination of programmable parameters. Such parameters may include, but are not limited to, parameters relating to frequency of pacing; other electrical stimulation therapies including anti-tachycardia pacing, cardioversion and shock therapies and neurostimulation therapies; arrhythmia detection algorithms; operation of other physiological sensors, such as blood or tissue oxygen sensors, pressure sensors, accelerometers, acoustical sensors or any other sensor operating in conjunction with the IMD or other IMD features that may be selectively enabled or disabled or controlled via programmable parameter settings selected by a user.

FIG. 1 is a conceptual diagram illustrating an example system 10 that may be used to monitor and/or provide therapy to heart 12 of patient 14. Patient 14 ordinarily, but not necessarily, will be a human. System 10 includes IMD 16, which is coupled to leads 18, 20, and 22, and programmer 24. IMD 16 may be, for example, an implantable pacemaker, cardioverter, and/or defibrillator that provides electrical signals to heart 12 via electrodes coupled to one or more of leads 18, 20, and 22. In accordance with one embodiment, IMD 16 may deliver LV-only pacing pulses via a plurality of pacing vectors that include at least one electrode on lead 20 in order to assess intervals between a LV pacing pulse and a sensed depolarization in the right ventricle (RV sense) to discriminate between capture and LOC, as will be described in greater detail below. IMD 16 is further capable of measuring a lead impedance with each of the pacing vectors and may provide the measured intervals and impedacnes, data derived therefrom or alerts or reports based thereon to programmer 24 via wireless telemetry.

Leads 18, 20, 22 extend into the heart 12 of patient 16 to sense electrical activity of heart 12 and/or deliver electrical stimulation to heart 12. In the example shown in FIG. 1, right ventricular (RV) lead 18 extends through one or more veins (not shown), the superior vena cava (SVC) and right atrium 26, and into right ventricle 28. Left ventricular (LV) coronary sinus lead 20 extends through one or more veins, the SVC, right atrium 26, and into the coronary sinus 30 to a region adjacent to the free wall of left ventricle 32 of heart 12. Right atrial (RA) lead 22 extends through one or more veins and the SVC, and into the right atrium 26 of heart 12. In some embodiments, coronary sinus lead 20 may additionally include electrodes positioned adjacent left atrium (LA) 36 for sensing and pacing in the LA.

IMD 16 may sense electrical signals attendant to the depolarization and repolarization of heart 12 via electrodes (not shown in FIG. 1) coupled to at least one of the leads 18, 20, 22. In some examples, IMD 16 provides pacing pulses to heart 12 based on the electrical signals sensed within heart 12. The configurations of electrodes used by IMD 16 for sensing and pacing may be unipolar or bipolar. IMD 16 may also provide defibrillation therapy and/or cardioversion therapy via electrodes located on at least one of the leads 18, 20, 22. IMD 16 may detect arrhythmias of heart 12, such as fibrillation of ventricles 28 and 32, and deliver defibrillation therapy to heart 12 in the form of electrical pulses. In some examples, IMD 16 may be programmed to deliver a progression of therapies, e.g., pulses with increasing energy levels, until a fibrillation of heart 12 is stopped. IMD 16 detects fibrillation employing one or more fibrillation detection techniques implemented in the device.

In some examples, programmer 24 may be a handheld device or a microprocessor based home monitor or bedside programming device. A user, such as a physician, technician, or other clinician, may interact with programmer 24 to communicate with IMD 16. For example, the user may interact with programmer 24 to retrieve physiological or diagnostic information from IMD 16. A user may also interact with programmer 24 to program IMD 16, e.g., select values for operational parameters of the IMD.

For example, the user may use programmer 24 to retrieve information from IMD 16 regarding the rhythm of heart 12, trends therein over time, or arrhythmic episodes. As another example, the user may use programmer 24 to retrieve information from IMD 16 regarding other sensed physiological parameters of patient 14, such as intracardiac or intravascular pressure, activity, posture, respiration, or thoracic impedance. As another example, the user may use programmer 24 to retrieve information from IMD 16 regarding the performance or integrity of IMD 16 or other components of system 10, such as leads 18, 20 and 22, or a power source of IMD 16. The user may use programmer 24 to program a therapy progression, select electrodes used to deliver defibrillation pulses, select waveforms for the defibrillation pulse, or select or configure a fibrillation detection algorithm for IMD 16. The user may also use programmer 24 to program aspects of other therapies provided by IMD 14, such as cardioversion or pacing therapies. A user interacting with programmer 24 may select programmable parameters and parameter settings for relative energy expenditure evaluation and enter a command for the energy expenditure evaluation to be performed.

In response to a command to perform the energy expenditure evaluation, or upon sending an interrogation command, programmer 24 receives data from IMD 16 for use in generating a text, table or graphic report displaying relative energy expenditure information for two or more programmable IMD parameter settings. Data received from IMD 16 may include capture threshold measurements, lead impedance measurements, history of frequency of pacing or other therapy delivery, up-to-date battery usage status, values of currently programmed IMD parameters and any other information needed to compute an estimated energy expenditure and predicted battery longevity. As will be described herein, the relative energy expenditure is computed in one embodiment in terms of differences in expected battery longevity for different programmable parameter settings or different combinations of programmable parameter settings. The necessary computations and generation of a relative energy expenditure report may be implemented in a controller or module which may be any combination of software, hardware or firmware implemented in the IMD, the programmer or a combination of both.

IMD 16 and programmer 24 communicate via wireless communication. Examples of communication techniques may include, for example, low frequency or radiofrequency (RF) telemetry using Bluetooth or MICS but other techniques are also contemplated. In some examples, programmer 24 may include a programming head that may be placed proximate to the patient's body near the IMD 16 implant site. In other embodiments, communication may be performed via distance telemetry without requiring the use of a programming head.

Figure 2:
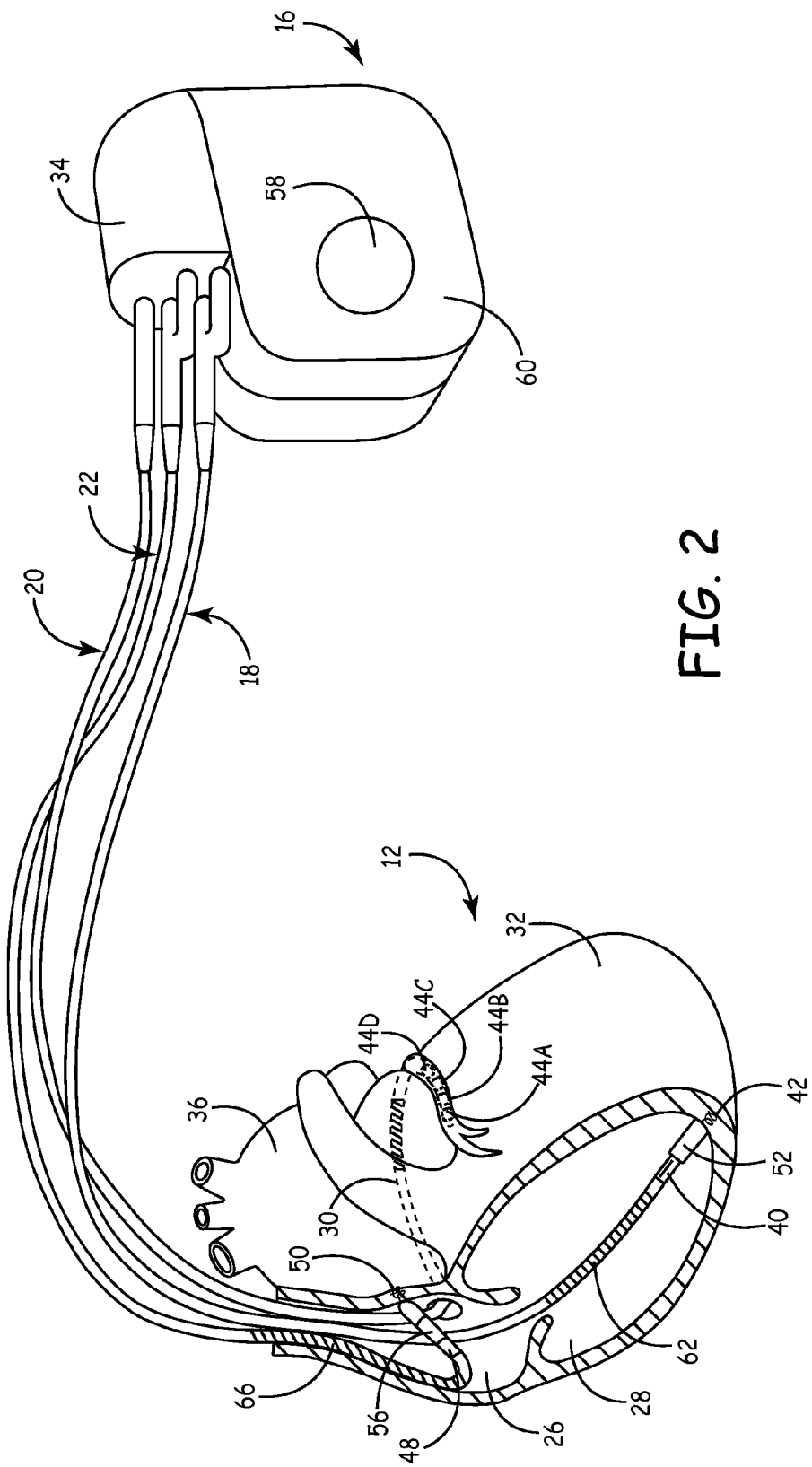
FIG. 2 is a conceptual diagram illustrating the implantable medical device (IMD) and leads of FIG. 1 in greater detail.

FIG. 2 is a conceptual diagram illustrating IMD 16 and leads 18, 20, and 22 of therapy system 10 in greater detail. Leads 18, 20, 22 are electrically coupled to a signal generator and a sensing module of IMD 16 via connector block 34.

Each of the leads 18, 20, 22 includes an elongated insulative lead body carrying one or more conductors. RV pacing and sensing electrodes 40 and 42 are located adjacent to a distal end of lead 18 and pacing and sensing electrodes 48 and 50 are located adjacent to a distal end of lead 22 for pacing and sensing in the RA 26. In some example configurations, lead 20 may be a quadripolar lead and, as such, include four electrodes, namely electrodes 44A-44D, which are located adjacent to a distal end of lead 20 for sensing and pacing in the LV. Electrodes 40, 44A-44D, and 48 may take the form of ring electrodes, and electrodes 42 and 50 may take the form of extendable helix tip electrodes mounted retractably within insulative electrode heads 52 and 56, respectively.

Leads 18 and 22 also include elongated electrodes 62 and 66 respectively, which may take the form of a coil. For example, lead 22 is shown to include a superior vena cava (SVC) coil electrode 66 for delivery of electrical stimulation, e.g., transvenous defibrillation. Lead 18 is shown to include an RV coil electrode 62 positioned in the right ventricle 28. In alternative embodiments, lead 18 may carry both an RV coil electrode 62 and an SVC coil electrode 66. Each of the electrodes 40, 42, 44A-44D, 48, 50, 62, and 66 is electrically coupled to a respective one of the conductors within the lead body of its associated lead 18, 20, 22, and thereby individually coupled to an electrical pulse generator and/or cardiac sensing module of IMD 16.

In some examples, as illustrated in FIG. 2, IMD 16 includes one or more housing electrodes, such as housing electrode 58, which may be formed integrally with an outer surface of hermetically-sealed housing 60 of IMD 16 or otherwise coupled to housing 60. In some examples, housing electrode 58 is defined by an uninsulated portion of an outward surface of housing 60. Other division between insulated and uninsulated portions of housing 60 may be employed to define two or more housing electrodes. In some examples, housing electrode 58 comprises substantially all of housing 60.

IMD 16 may sense electrical signals attendant to the depolarization and repolarization of heart 12 via electrodes 40, 42, 44A-44D, 48, 50, 58, 62, and 66. The electrical signals are conducted to IMD 16 via the respective leads 18, 20, 22, or in the case of housing electrode 58, a conductor coupled to the housing electrode. IMD 16 may sense such electrical signals via any bipolar combination of electrodes 40, 42, 44A-44D, 48, 50, 58, 62, and 66. Furthermore, any of the electrodes 40, 42, 44A-44D, 48, 50, 58, 62, and 66 may be used for unipolar sensing in combination with housing electrode 58.

IMD 16 delivers pacing pulses via any bipolar or unipolar combination of electrodes 40, 42, 44A-44D, 48, 50, 58, 62, and 66 to produce depolarization of cardiac tissue of heart 12. For example, electrodes 40, 42, and may be used to deliver bipolar RV pacing to heart 12. Electrodes 44A-44D may be used to deliver bipolar LV pacing to heart 12, and electrodes 48 and 50 may be used to deliver bipolar RA pacing to heart 12.

Furthermore, IMD 16 may deliver cardioversion or defibrillation pulses to heart 12 via any combination of elongated electrodes 62 and 66 and housing electrode 58. In some embodiments, the large surface area coil electrodes 62 and 66 may be used in combination with any of electrodes 40, 42, 44A-44D 48 and 50 for providing, for example, unipolar sensing vectors.

The configuration of therapy system 10 illustrated in FIGS. 1 and 2 is merely one example. In other examples, a therapy system may include epicardial leads and/or patch electrodes instead of or in addition to the transvenous leads 18, 20, 22 illustrated in FIGS. 1 and 2. Further, IMD 16 need not be implanted within patient 14. In examples in which IMD 16 is not implanted in patient 14, IMD 16 may deliver defibrillation pulses and other therapies to heart 12 via percutaneous leads that extend through the skin of patient 14 to a variety of positions within or outside of heart 12.

In addition, in other examples, IMD system may include any suitable number of leads coupled to IMD 16, and each of the leads may extend to any location within or proximate to heart 12. For example, other examples of therapy systems may include three transvenous leads located as illustrated in FIGS. 1 and 2, and an additional lead located within or proximate to left atrium 36. In still other examples, IMD 16 may be embodied without the use of transvenous leads utilizing electrodes incorporated along housing 60 and/or leads extending extravascularly from IMD 16 to position electrodes subcutaneously or submuscularly relative to heart 12 for sensing cardiac signals and delivering electrical pulses to heart 12.

One example of a "subcutaneous" device that does not require the use of transvenous leads is generally disclosed in U.S. Pat. No. 7,894,894 (Stadler et al.), hereby incorporated herein by reference in its entirety.

Two or more electrodes, and the polarity of the electrodes, define a vector, or path, for delivering pacing pulses to heart 12. As described above, there are numerous vectors that may be used to deliver pacing pulses to heart 12. For example, various combinations of the electrodes on a single quadripolar lead, i.e., a lead with four electrodes on the lead, such as lead 20, as well as unipolar combinations of the lead electrodes with a housing electrode or for example a coil electrode, may provide sixteen different vectors that may be used to deliver pacing pulses to a chamber of heart 12 that the lead is within or on. Testing each vector in order to determine which vector sufficiently captures the heart without unnecessarily depleting the battery, e.g., by pacing at the lowest possible pulse amplitude that captures the heart, may be a time-consuming process.

Furthermore, the battery expenditure will also depend on the lead impedance associated with a candidate pacing vector. So while a clinician may select a pacing vector based on a lowest capture threshold, this pacing vector may be associated with relatively lower lead impedance and not necessarily result in the lowest energy expenditure over time. Without relative energy expenditure information, the clinician cannot make an informed decision when selecting pacing parameters for achieving both a desired therapeutic benefit and battery longevity. Using the techniques of this disclosure, a clinician may quickly determine one or more electrode combinations of one or more leads of an implantable medical device that result in acceptable energy expenditure for pacing therapy delivery.

Figure 3:
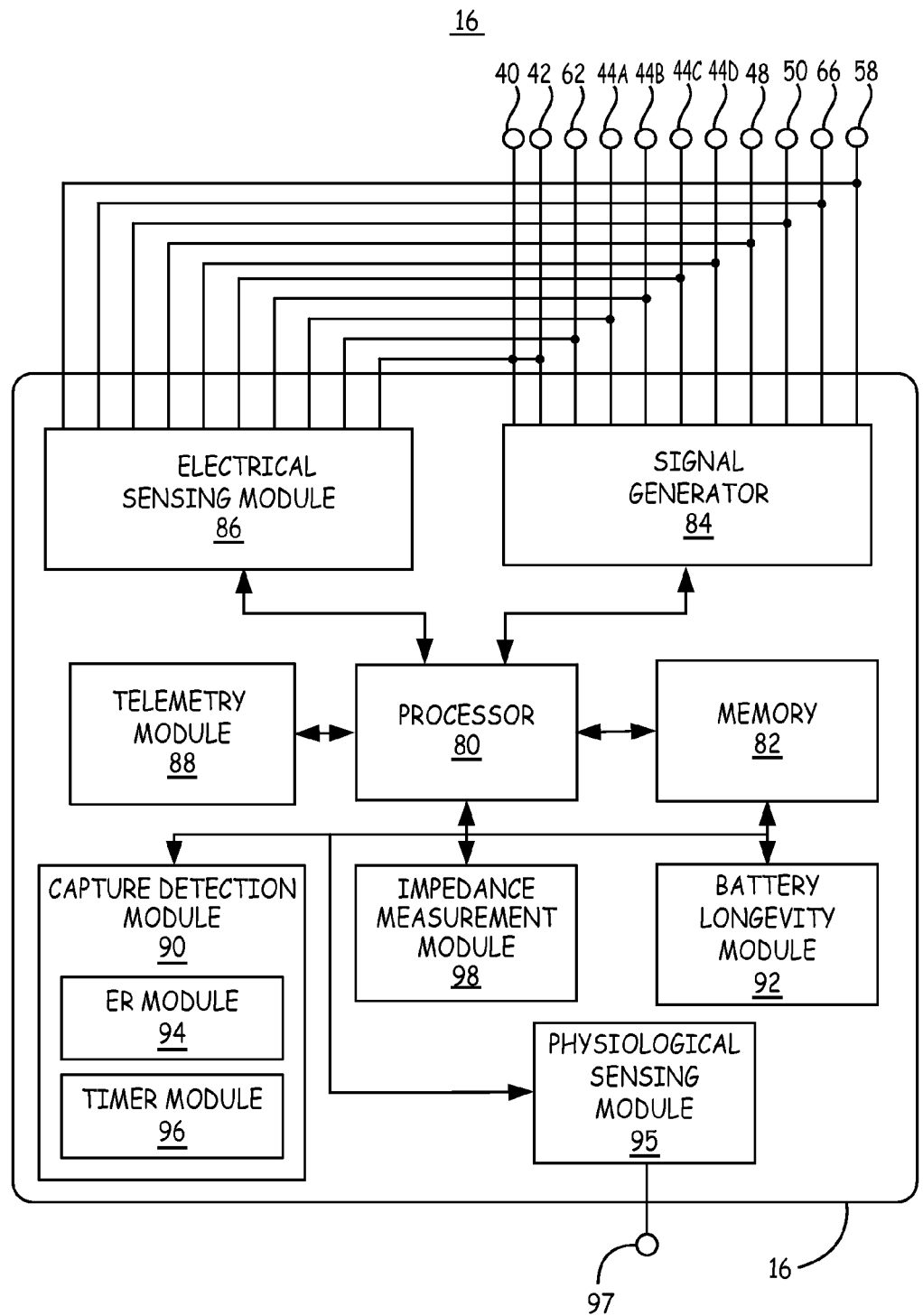
FIG. 3 is a block diagram illustrating one example configuration of the IMD of FIG. 2.

FIG. 3 is a block diagram illustrating one example configuration of IMD 16. In the example illustrated by FIG. 3, IMD 16 includes a processor 80, memory 82, signal generator 84, electrical sensing module 86, and telemetry module 88. IMD 16 further includes capture detection module 90, which itself includes evoked response detection module 94 and timer module 96 for determining capture thresholds. IMD 16 additionally includes battery longevity module 92, physiological sensing module 95 coupled to at least one associated physiological sensor 97, and impedance measurement module 98.

Memory 82 may include computer-readable instructions that, when executed by processor 80, cause IMD 16 and processor 80 to perform various functions attributed throughout this disclosure to IMD 16, processor 80, capture detection module 90, impedance measurement module 98 or battery longevity module 92. The computer-readable instructions may be encoded within memory 82. Memory 82 may comprise computer-readable storage media including any volatile, non-volatile, magnetic, optical, or electrical media, such as a random access memory (RAM), read-only memory (ROM), non-volatile RAM (NVRAM), electrically-erasable programmable ROM (EEPROM), flash memory, or any other digital media.

Processor 80 may include any one or more of a microprocessor, a controller, a digital signal processor (DSP), an application specific integrated circuit (ASIC), a field-programmable gate array (FPGA), or equivalent discrete or integrated logic circuitry. In some examples, processor 80 may include multiple components, such as any combination of one or more microprocessors, one or more controllers, one or more DSPs, one or more ASICs, or one or more FPGAs, as well as other discrete or integrated logic circuitry. The functions attributed to processor 80 herein may be embodied as software, firmware, hardware or any combination thereof. In one example, capture detection module 90, evoked response detection module 94, and timer module 96, impedance measurement module, and battery longevity module 92 may, at least in part, be stored or encoded as instructions in memory 82 that are executed by processor 80.

Processor 80 controls signal generator 84 to deliver stimulation therapy, e.g., cardiac pacing or cardiac resynchronization therapy (CRT), to heart 12 according to a selected one or more therapy programs, which may be stored in memory 82. Signal generator 84 is electrically coupled to electrodes 40, 42, 44A-44D, 48, 50, 58, 62, and 66, e.g., via conductors of the respective lead 18, 20, 22, or, in the case of housing electrode 58, via an electrical conductor disposed within housing 60 of IMD 16. Signal generator 84 is configured to generate and deliver electrical stimulation therapy to heart 12 via selected combinations of electrodes 40, 42, 44A-44D, 48, 50, 58, 62, and 66. In some examples, signal generator 84 is configured to deliver cardiac pacing pulses.

Signal generator 84 may include a switch module (not shown) and processor 80 may use the switch module to select, e.g., via a data/address bus, which of the available electrodes are used to deliver pacing pulses. Processor 80 may also control which of electrodes 40, 42, 44A-44D, 48, 50, 58, 62, and 66 is coupled to signal generator 84 for delivering stimulus pulses, e.g., via the switch module. The switch module may include a switch array, switch matrix, multiplexer, or any other type of switching device suitable to selectively couple a signal to selected electrodes.

Electrical sensing module 86 monitors signals from at least one of electrodes 40, 42, 44A-44D, 48, 50, 58, 62, or 66 in order to monitor electrical activity of heart 12. Electrical sensing module 86 may also include a switch module to select which of the available electrodes are used to sense the cardiac activity. In some examples, processor 80 selects the electrodes that function as sense electrodes, or the sensing vector, via the switch module within electrical sensing module 86.

Electrical sensing module 86 includes multiple detection channels, each of which may be selectively coupled to respective combinations of electrodes 40, 42, 44A-44D, 48, 50, 58, 62, or 66 to detect electrical activity of a particular chamber of heart 12. Each detection channel may comprise an amplifier that outputs an indication to processor 80 in response to sensing of a cardiac depolarization, in the respective chamber of heart 12. In this manner, processor 80 may detect the occurrence of R-waves and P-waves in the various chambers of heart 12.

Memory 82 stores intervals, counters, or other data used by processor 80 to control the delivery of pacing pulses by signal generator 84. Such data may include intervals and counters used by processor 80 to control the delivery of pacing pulses to one or both of the left and right ventricles for CRT. The intervals and/or counters are, in some examples, used by processor 80 to control the timing of delivery of pacing pulses relative to an intrinsic or paced event, e.g., in another chamber.

In one example, capture detection module 90 uses signals from electrical sensing module 86 to detect capture and/or LOC when signal generator 84 delivers a pacing pulse. Via the switching module, processor 80 may control which of electrodes 40, 42, 44A-44D, 48, 50, 58, 62, and 66 is coupled to electrical sensing module 86 to detect a depolarization in a second chamber, e.g., the RV, subsequent to the delivery of a pacing pulse to a first chamber, e.g., the LV, for the determination of whether the pacing pulse captured the first chamber. Processor 80 may also control which of electrodes 40, 42, 44A-44D, 48, 50, 58, 62, and 66 is coupled to electrical sensing module 86 to detect an evoked electrical response in the first chamber to the pacing pulse in the first chamber. Memory 82 may store predetermined intervals or voltage thresholds which define whether a detected signal has an adequate magnitude and is appropriately timed relative to the pacing pulse to be considered a depolarization in the second chamber indicative of capture or an evoked response in the first chamber. In some examples, a channel of electrical sensing module 86 used to detect capture comprises a sense amplifier which provides an indication to processor 80 when a cardiac signal has an adequate magnitude or other circuitry for detecting a cardiac signal feature indicative of a cardiac depolarization and therefore useful in detecting successful capture.

Processor 80 controls the selection of electrode configurations for delivering pacing pulses and for detecting capture and/or loss of capture and for measuring lead impedances. Processor 80, for example, may communicate with signal generator 84 to select two or more stimulation electrodes in order to generate one or more pacing pulses for delivery to a selected chamber of heart 12. Processor 80 may also communicate with electrical sensing module 86 to select two or more sensing electrodes for capture detection based on the chamber to which the pacing pulse is delivered by signal generator 84.

Capture detection module 90, in the example of FIG. 3, is capable of detecting capture and LOC during capture detection tests. Capture detection module 90 uses timer module 96 to determine when to deliver pacing pulses and to determine conduction times between chambers of the heart. In addition, as seen in FIG. 3, capture detection module 90 further includes evoked response detection module 94 for detecting the amplitude and timing of an evoked response which may be used additionally or alternatively for detecting capture or LOC.

Using certain techniques of this disclosure, capture detection module 90 may determine pacing capture thresholds for each of a plurality of pacing vectors by, for each of the vectors, delivering pacing pulses at various voltage levels, measuring a ventricular conduction times between the LV pacing pulses and RV sensed R-waves (LVP-RVS conduction time) in response to each of the pacing pulses, and determining a voltage at which capture or LOC occurs based on the measured conduction times. Briefly, the pacing capture test techniques of this disclosure may include pacing an atrium, measuring an intrinsic atrioventricular (AV) interval of a patient in response to the delivered pace, delivering a pacing pulse at a voltage to the left ventricle of the heart during the intrinsic AV interval, determining whether capture occurred as a result of the pacing pulse, and iteratively adjusting the voltage (or another parameter affecting pacing pulse energy) and delivering pacing pulses at the adjusted voltages (or other adjusted parameters) in order to determine a particular voltage (or other parameter setting) at which capture or LOC occurs.

A capture threshold may be determined for each one of multiple candidate pacing vectors according to numerous techniques. In one embodiment, the techniques disclosed in U.S. patent application Ser. No. 12/909,057 are implemented for measuring multiple pacing vector capture thresholds using a multipolar LV lead. U.S. patent application Ser. No. 12/909,057, filed on Oct. 21, 2010, and entitled "CAPTURE THRESHOLD MEASUREMENT FOR SELECTION OF PACING VECTOR", is commonly assigned and hereby incorporated herein by reference in its entirety.

Before delivering any pacing pulses, a basic stability test may be performed on the patient. The basic stability test monitors the patient's current heart rhythm in order to verify the stability and rate of the patient's heart. An AV measurement cycle is performed after the successful completion of the basic stability test. The time from the atrial depolarization to the right ventricular depolarization to be measured when no or subthreshold pacing of the ventricles is delivered. Following the basic stability test and AV measurement cycle, processor 80 controls signal generator 84 to overdrive the patient's heart rate, e.g., by using shorter A-V pacing intervals in order to lower the chances of competing with intrinsic depolarizations during pacing. When LV-only pacing is delivered, for LV capture to have occurred as a result of an LV-only pace, the LVP-RVS time must be shorter than the A-RVS minus the A to LVP (or zero-volt LVP-RVS) time determined during the AV measurement cycle, as described in detail in the '057 application.

After the pacing pulse is delivered, electrical sensing module 86 and capture detection module 90 determine whether there is evidence of capture. Electrical sensing module 86 and capture detection module 90 determine the time at which a corresponding depolarization on the right side of the heart occurs (RVS) and, based on this time, determine whether capture has occurred in the LV in response to an LV pacing pulse using the candidate pacing vector.

Figure 4A:
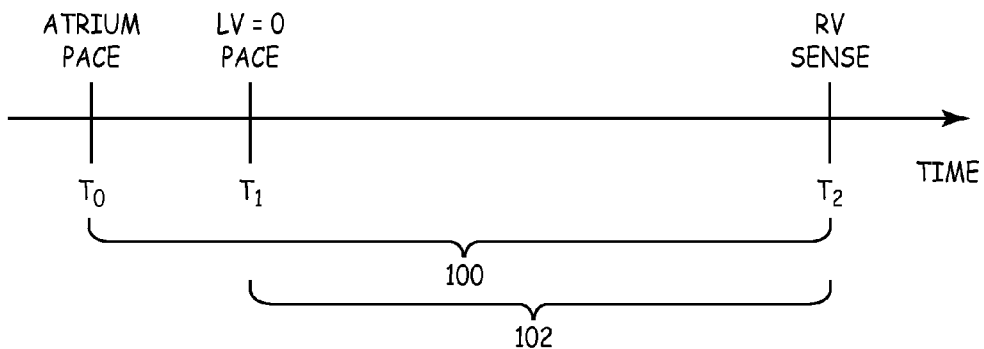
FIGS. 4A-4C are conceptual timing diagrams illustrating techniques for determining an inter-chamber pace to sense interval.
Figure 4B:
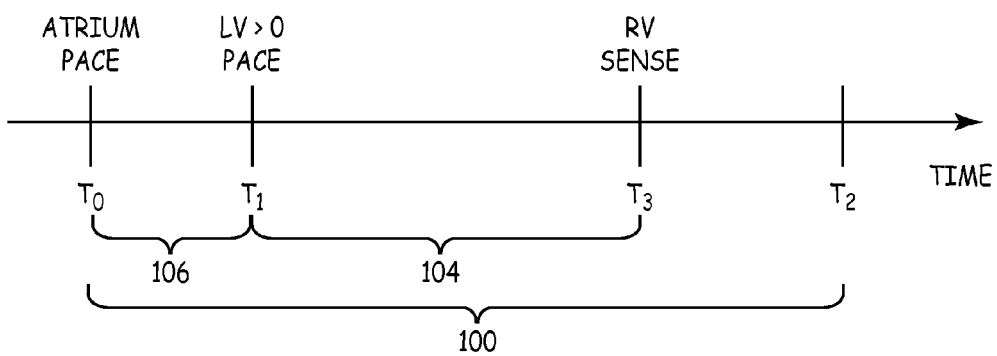
Figure 4C:
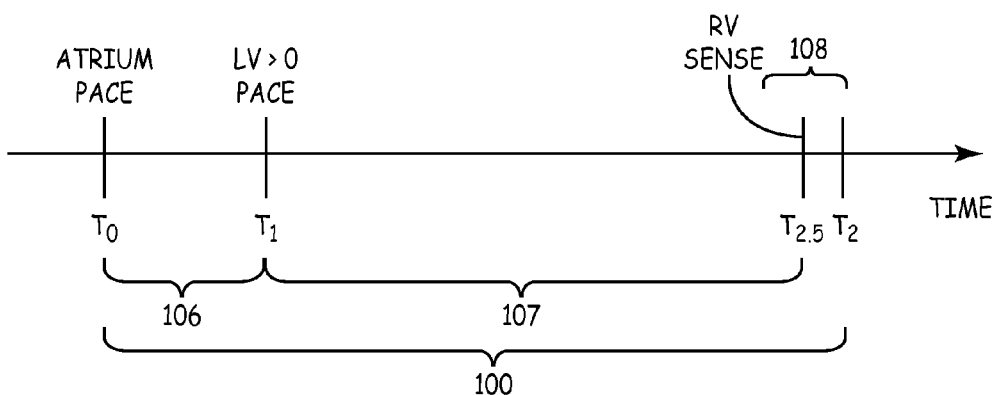

FIGS. 4A-4C are conceptual timing diagrams illustrating techniques for determining an inter-chamber pace to sense interval. FIG. 4A depicts a simplified A-RVS timing diagram determined during the AV measurement cycle described above. In FIG. 4A, the right atrium is paced at time $T_0$. A predetermined time later, at time $T_1$, the left ventricle is paced with a 0V pacing pulse. Finally, the right ventricle is sensed at time $T_2$. The A-RVS time $T_2-T_0$, shown at 100, is the time between atrial depolarization and the right ventricular depolarization and serves as the baseline for determining whether a non-zero LV pacing pulse captures. The LVP (zero volt)-RVS time $T_2-T_1$, shown at 102, is the time between the left ventricle 0V pacing pulse and the right ventricular depolarization and serves as an alternate baseline for determining whether a non-zero LV pacing pulse captures.

FIG. 4B depicts a simplified LVP-RVS conduction time timing diagram for a non-zero pacing pulse delivered to the left ventricle. In FIG. 4B, the right atrium is paced at time $T_0$. A predetermined time later, at time $T_1$, the left ventricle is paced with a non-zero pacing pulse. Finally, the right ventricle is sensed at time $T_3$. In order to determine whether the pacing pulse, i.e., LVP, captured, the time between the left ventricle pacing pulse, $T_1$, and the RV sense, $T_3$, shown at 104, plus the predetermined time between the right atrium pace and the LVP, shown at 106, must be less than the A-RVS time, shown at 100 and above in FIG. 4A, determined during the AV measurement cycle. In other words, time $T_3-T_0$ in FIG. 4B, shown as 104, 106, must be less than the A-RVS time $(T_2-T_0)$ in FIG. 4B, shown as 100, in order for capture to have occurred. Alternatively, in order to determine whether the LV pacing pulse captured, the time between the left ventricle pacing pulse, T1, and the RV sense, T3, shown at 104, must be less than the LVP (zero volt)-RVS time $T_2-T_1$, shown at 102 in FIG. 4A, determined during the AV measurement cycle.

FIG. 4C depicts a simplified LVP-RVS conduction time timing diagram for a non-zero pacing pulse delivered to the left ventricle where capture does not occur. In FIG. 4C, the right atrium is paced at time $T_0$. A predetermined time later, at time $T_1$, the left ventricle is paced with a non-zero pacing pulse. Finally, the right ventricle is sensed at time $T_{2.5}$. In order to determine whether the pacing pulse, i.e., LVP, captured, the time between the left ventricle pacing pulse, $T_1$, and the RV sense, $T_{2.5}$, shown at 107, plus the predetermined time between the right atrium pace and the LVP, shown at 106, must be less than the A-RVS time, shown at 100, determined during the AV measurement cycle. In other words, time $T_3-T_0$ in FIG. 4C, shown as 106 and 107, must be less than the A-RVS time $(T_2-T_0)$, shown as 100, in order for capture to have occurred.

In the example depicted in FIG. 4C, the time between the left ventricle pacing pulse, $T_1$, and the RV sense, $T_{2.5}$, shown at 107, plus the predetermined time between the right atrium pace and the LVP, shown at 106, is slightly less than the A-RVS time, shown at 100, determined during the AV measurement cycle. Nevertheless, capture may not have occurred. In one example aspect of the techniques of this disclosure, a threshold time interval may be set, e.g., by a user, such that in order for capture detection module 90 to determine that capture occurred, the RV sense must be outside of that threshold time interval. For example, in FIG. 4C, capture detection module 90 may utilize a settable threshold time interval margin 108 based on the A-RVS time 100 less a margin 108, e.g., about 30 ms to about 40 ms, to determine whether capture occurred. If capture detection module 90 determines that the RV sense occurred within a non-capture window, shown as threshold time interval 108, capture detection module 90 determines loss of capture. For example, in FIG. 4C, the RV sense occurred at time $T_{2.5}$. However, RV sense time $T_{2.5}$ is within the non-capture window, shown as threshold time interval 108. Thus, capture detection module 90 determines loss of capture for that LV pacing pulse.

To summarize, in some embodiments, capture detection module 90 determines loss of capture if either of the following scenarios occurs: 1) if the first RV sense after the LV-only pace occurs at or after the RV sense time $T_2$ determined during the AV measurement cycle described above with respect to FIG. 4A, or 2) if the first RV sense after the LV-only pace is prior to the RV sense time $T_2$ determined during the AV measurement cycle described above with respect to FIG. 4A, but within a non-capture window, shown as threshold time interval 108 in FIG. 4C. Capture detection module 90 determines that capture occurred if the first RV sense after the LV-only pace is prior to time $T_2$ determined during the AV measurement cycle described above with respect to FIG. 4A and not within non-capture window, shown as threshold time interval 108 in FIG. 4C, and if the RV sense is determined to be a physiological sense.

It should be noted that if there was no RVS, or there was an extremely long A-RVS time in the AV test, then a default maximum value might be used to set the start of the non-capture window. The non-capture window may be a set amount of time before the RV sense time $T_2$ determined during the AV measurement cycle described above with respect to FIG. 4A.

Referring again to FIG. 3, if there is evidence that the pacing pulse captured, e.g., as determined by the LVP-RVS conduction times and/or by detection of an evoked response in the LV, then capture detection module 90 selects another voltage at which to deliver a pacing pulse, using the same vector, to the left ventricle of the patient's heart that is less than the initial voltage until there is no evidence of LV capture (i.e., LOC).

If there was no evidence of capture at the initially selected voltage, then the pacing capture threshold test increases the voltage to a maximum value of the range of voltages, e.g., 6V, and through a range of voltages between the maximum voltage and the initial voltage, iteratively decreases the maximum voltage and delivers pacing pulses to the left ventricle until evidence of LOC. The pacing capture threshold test is attempting to determine the minimum voltage that will capture, which will reduce power consumption and extend battery life.

It should be noted that the iterative technique described above is only one possible search method for determining a capture threshold. In other examples, processor 80 may control signal generator 84 to iteratively increase the voltage if the initial voltage does not capture. In another example, processor 80 may control signal generator 84 to begin at a voltage that captured most recently and increase or decrease the voltage from that voltage. Once the capture threshold is identified for a first candidate vector, the capture threshold test is repeated for each additional candidate vector. Since each electrode vector will probably have slightly different mean thresholds, an initial pulse amplitude (or pulse width) for each pacing vector may be set differently for each candidate vector based on a previous threshold measurement or on data from clinical studies of a patient population. For example, electrode 44D positioned near the base of the LV will tend to have a higher capture threshold when used as the pacing cathode than a pacing vector using a more distal electrode 44A as the pacing cathode. As such, pacing vectors including 44D as a cathode may have a higher initial starting pulse amplitude during an iterative capture threshold search technique than an initial pulse amplitude used for a pacing vector using 44A as the cathode.

In another example implementation, electrical sensing module 86 and capture detection module 90 determine whether capture has occurred based on the LVP-RVS conduction times, as described above, as well as the evoked response in the LV. In particular, electrical sensing module 86 and evoked response detection module 94 of capture detection module 90 determine whether there has been an evoked response by measuring the amplitude of the response in the LV as well as time between the LVP and the evoked response in the LV. In order for capture to have occurred, the time between the LVP and the evoked response in the LV should be within a prescribed window, and the amplitude of the response should be greater than some threshold value. Processor 80 may retrieve the previously stored threshold value from memory 82 and capture detection module 90 may compare the measured amplitude of the response to the threshold value. In addition, for each vector tested at each particular voltage, processor 80 may store the measured LV response amplitude along with the time between the LVP and the evoked response in the LV as data in memory 82. In such an example implementation, the pacing capture threshold test may conclude that capture has occurred for a tested vector at a particular voltage if the following occur: the LVP-RVS conduction time is less than the A-RVS time and the time between the LVP and the evoked response in the LV is within the prescribed evoked response window; and the amplitude of the response in the LV is above the threshold value.

Capture detection module 90 may output to a programmer 24 (FIG. 1) a list of vectors and the capture or loss of capture voltages associated with each vector. In some examples, capture detection module 90 may rank or order the tested vectors, e.g., in order of increasing voltage amplitude. The clinician may specify the order in which the vectors should be listed, e.g., high voltage to low voltage, low voltage to high voltage. In addition, capture detection module 90 may sort the tested vectors according to characteristics, e.g., impedance and voltage, provided by the clinician, for example. In some examples, capture detection module 90 may automatically select tested vectors based on previously defined criteria.

Figure 5:
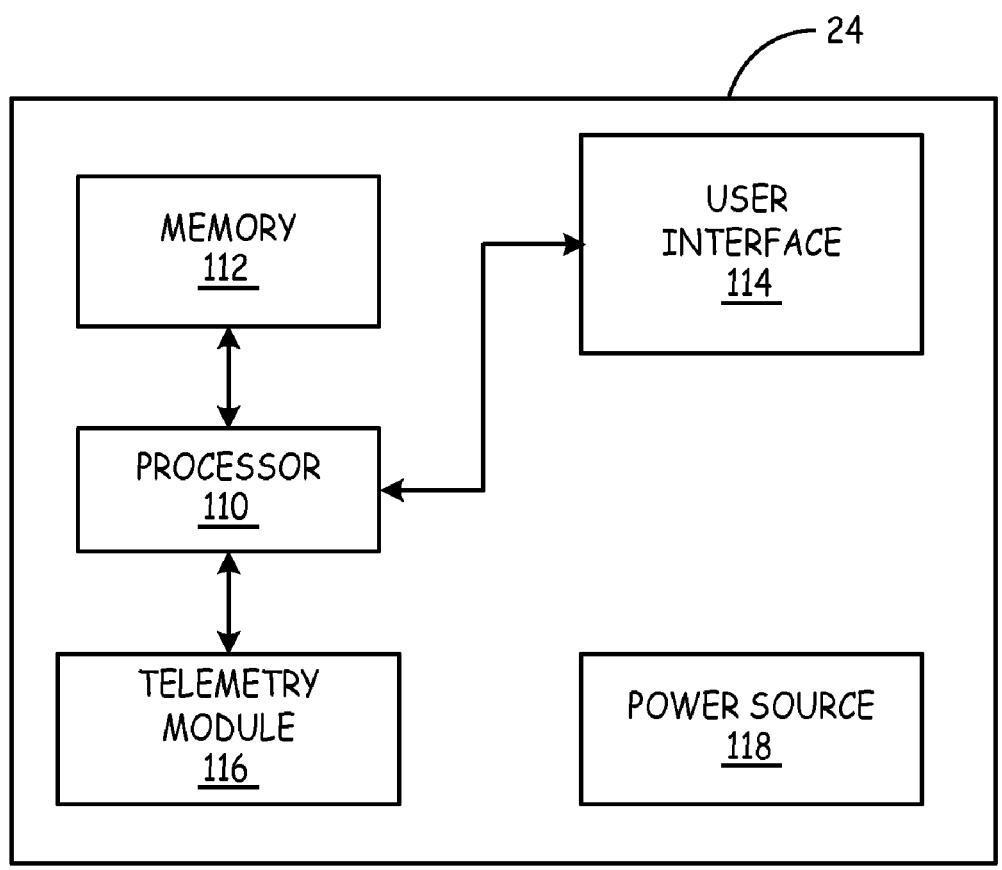
FIG. 5 is functional block diagram illustrating an example configuration of programmer.

In one example implementation, a processor may control a user interface, e.g., user interface 114 of programmer 24 of FIG. 5, to provide a "check box" or some other graphic which may receive input from a user. Using the check box, a clinician may provide input to programmer 24 if undesired muscle and/or nerve stimulation occurred for a particular vector. In other words, the clinician may tag a vector if undesirable muscle and/or nerve stimulation occurred. Providing input in this manner may allow tagged vectors to be ranked lower than untagged vectors. Tagged vectors may be communicated back to the IMD, e.g., via telemetry module 116 of programmer 24 of FIG. 5, so that the IMD would be able to provide that information to other programmers at later dates, thereby allowing the clinicians the option to exclude vectors with a history of undesired stimulation in future test runs.

In other example implementations, the clinician may specify that only some of the available vectors should be tested. For example, for a quadripolar lead, although there are sixteen possible vectors, a clinician may only be interested in the ten most commonly used vectors, or some other subset of the total available vectors. As such, the clinician may specify, e.g., using programmer 24, the particular vectors that should be tested for pacing capture thresholds. In some examples, clinicians may save their preferred vectors for a given lead, and then load and run a test using those preferred vectors.

In addition to capture threshold measurements, processor 80 and impedance measurement module 98 perform impedance measurements for each candidate pacing vector during the pacing capture threshold tests. Processor 80 may control impedance measurement module 98 to perform the impedance measurements tests in parallel or simultaneously with the pacing capture threshold tests. These impedance values may be transmitted and displayed along with the pacing capture threshold values to the clinician, e.g., via programmer 24, at the end of test. Impedance measurement module 98 will generally include drive signal circuitry for delivering a current signal and recording circuitry for measuring the resulting voltage signal across a measurement pair of electrodes. Alternatively, the drive signal may be delivered by signal generator 84. The voltage signal measured by the measurement pair of electrodes may be used directly or converted to an impedance measurement using the known drive current signal. As such, impedance measurement module 98 may operate in combination with signal generator 84, electrical sensing module 86, processor 80 and memory 82 for obtaining lead impedance measurements.

Examples of lead impedance measurements that may be implemented or adapted for use in conjunction with the methods disclosed herein are generally described in U.S. Pub. No. 2008/0077189 (Ostroff), U.S. Pat. No. 5,897,577 (Cinbis), U.S. Pat. No. 5,814,088 (Paul, et al), and U.S. Pub. No. 2009/0156957 (Linder, et al). Practice of the methods described herein for providing relative energy expenditure information is not limited to any particular lead impedance measurement method or any particular capture threshold method as long as the methods are used in a consistent manner between candidate pacing vectors during an energy expenditure analysis algorithm to yield comparable results when used for computing estimated energy expenditure.

In one example implementation, a clinician may specify that only vectors having certain qualities, e.g., certain thresholds and impedances, should be displayed upon completion of the energy expenditure evaluation. For example, a clinician may specify, e.g., using programmer 24, that only vectors having capture thresholds that are less than about 3V and having impedances of greater than about 500 ohms should be displayed.

Processor 80 and battery longevity module 92 utilize the capture threshold and lead impedance data to compute an estimated energy expenditure for each of the candidate pacing vectors. Additionally, as further described below, currently programmed pacing parameters stored in memory 82, historical IMD performance data stored in memory 82, other parameters identified and input by a user using programmer 24, or other measurements performed by IMD 16, such as battery-related measurements, may be used in computing an estimated energy expenditure for the multiple pacing vector selections.

In some embodiments, IMD 16 may be embodied to include physiological signal sensing module 95 for processing and analyzing a signal received from at least one other physiological signal transducer 97, other than the electrodes used for sensing and measuring cardiac electrical signals and lead impedances. Among the other types of physiological signal transducers that may be used in conjunction with an IMD are, for example, pressure sensors, accelerometers, activity sensors, posture sensors, and oxygen sensors. Other physiological signals may be processed and analyzed for use in detecting a need for therapy and monitoring a response to therapy. In some embodiments, a user interacting with programmer 24 (FIG. 1), is able to select control parameters relating to the function and use of physiological sensor 97 and sensing module 95 to be evaluated in a relative energy expenditure analysis.

Telemetry module 88 includes any suitable hardware, firmware, software or any combination thereof for communicating with another device, such as programmer 24 (FIG. 1). Under the control of processor 80, telemetry module 88 may receive downlink telemetry from and send uplink telemetry to programmer 24 with the aid of an antenna, which may be internal and/or external. Processor 80 provides data to be uplinked to programmer 24 and receives data from programmer 24 via telemetry module 88.

FIG. 5 is functional block diagram illustrating an example configuration of programmer 24. As shown in FIG. 5, programmer 24 may include a processor 110, memory 112, user interface 114, telemetry module 116, and power source 118. Programmer 24 may be a dedicated hardware device with dedicated software for programming of IMD 16. Alternatively, programmer 24 may be an off-the-shelf computing device running an application that enables programmer 24 to program IMD 16 and exchange data with IMD 16.

A user may use programmer 24 to select therapy programs (e.g., sets of stimulation parameters), generate new therapy programs, modify therapy programs through individual or global adjustments or transmit the new programs to a medical device, such as IMD 16 (FIG. 1). The clinician may interact with programmer 24 via user interface 114, which may include display to present a graphical user interface to a user, and a keypad, mouse, or other mechanism(s) for receiving input from a user. The user, e.g., a clinician, may define or select pacing vectors to be tested and/or input vector impedance values via user interface 114. In some embodiments, a user is able to establish via user interface 114 programmable parameter values or sets of programmable parameters for comparative analysis of relative energy expenditure. For example, the user may select LV pacing vectors as a programmable parameter for comparative analysis of relative energy expenditure. The programmer 24 may, in cooperation with IMD 16, generate and present energy expenditure information relating to all available LV pacing vectors. Alternatively, the user may select which values of a given programmable parameter, for example which specific vectors of the available LV pacing vectors, are to be included in the analysis.

User interface 114 may display the vectors to be tested as well as the results of the energy expenditure calculations, pacing capture threshold tests and impedance measurements to the clinician. User interface 114 may display each vector tested, and its associated energy expenditure, in some order that the clinician may select or adjust. The results of the tests and energy usage estimations, which may include or be represented as battery longevity calculations, may also be stored within memory 112.

Processor 110 can take the form one or more microprocessors, DSPs, ASICs, FPGAs, programmable logic circuitry, or the like, and the functions attributed to processor 110 herein may be embodied as hardware, firmware, software or any combination thereof. Memory 112 may store instructions that cause processor 110 to provide the functionality ascribed to programmer 24 herein, and information used by processor 110 to provide the functionality ascribed to programmer 24 herein. Memory 112 may include any fixed or removable magnetic, optical, or electrical media, such as RAM, ROM, CD-ROM, hard or floppy magnetic disks, EEPROM, Flash memory, or the like. Memory 112 may also include a removable memory portion that may be used to provide memory updates or increases in memory capacities. A removable memory may also allow patient data to be easily transferred to another computing device, or to be removed before programmer 24 is used to program therapy for another patient.

Programmer 24 may communicate wirelessly with IMD 16, such as using RF communication or proximal inductive interaction. This wireless communication is possible through the use of telemetry module 116, which may be coupled to an internal antenna or an external antenna. An external antenna that is coupled to programmer 24 may correspond to a programming head that may be placed over IMD 16. Telemetry module 116 may be similar to telemetry module 88 of IMD 16 (FIG. 3).

Telemetry module 116 may also be configured to communicate with another computing device via wireless communication techniques, or direct communication through a wired connection. Examples of local wireless communication techniques that may be employed to facilitate communication between programmer 24 and another computing device include RF communication according to the 802.11 or Bluetooth specification sets, infrared communication, e.g., according to the IrDA standard, or other standard or proprietary telemetry protocols. In this manner, other external devices may be capable of communicating with programmer 24 without needing to establish a secure wireless connection. An additional computing device in communication with programmer 24 may be a networked device such as a server capable of processing information retrieved from IMD 16.

In some examples, processor 110 of programmer 24 and/or one or more processors of one or more networked computers may perform all or a portion of the techniques described herein with respect to processor 80 and IMD 16. For example, processor 110 or another processor may receive voltages or currents measured by IMD 16 to calculate impedance measurements, or may receive impedance measurements from IMD 16. Processor 110 or another processor may be configured determine relative energy expenditure and battery longevity values using any of the techniques described in this disclosure. Power source 118 delivers operating power to the components of programmer 24.

Processor 110 may be configured to compute an estimated battery longevity and relative energy expenditure of different pacing vectors using measured capture thresholds and impedance measurements for each candidate vector. Processor 110, in cooperation with memory 112 and a display included in user interface 114 generates a graphical display or report of relative energy expenditure for different pacing vectors to allow a clinician to quickly evaluate the expected battery longevity associated with different pacing vector selections. Alternatively, processor 110 receives via telemetry module 116 estimated battery longevity data computed by processor 80 of IMD 16 and determines and displays relative energy expenditure data for review by a clinician.

As further described below, computation and display of relative energy expenditures may additionally or alternatively be provided for other programmable parameters or features of the IMD 16. For example, other programmable settings may relate to therapy delivery options or physiological signal monitoring for detecting a patient condition or monitoring a physiological condition or a physiological response to therapy delivery.

Figure 6:
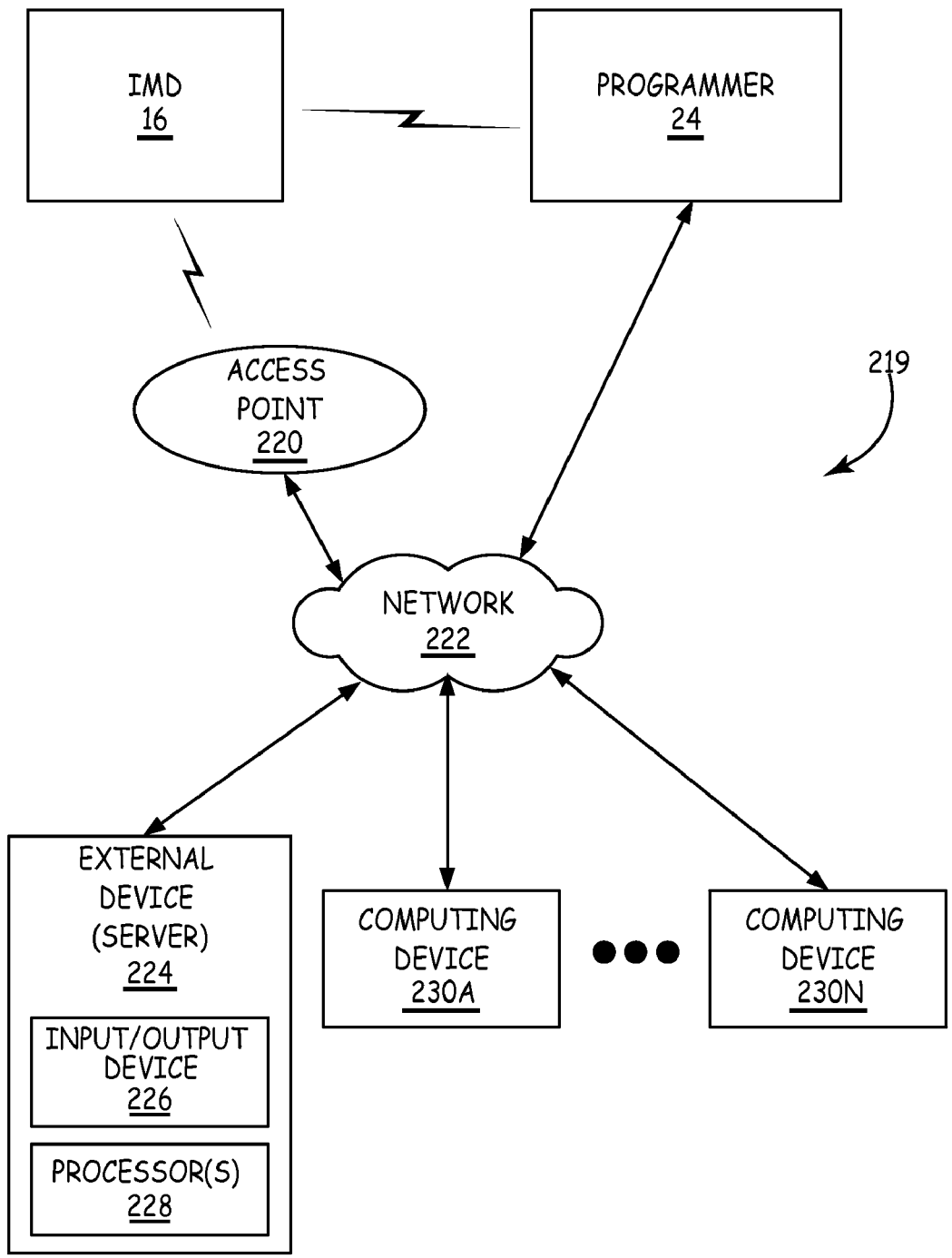
FIG. 6 is a block diagram illustrating an example system that includes an external device and one or more computing devices that are coupled to the IMD and programmer shown in FIG. 5 via a network.

FIG. 6 is a block diagram illustrating an example system 219 that includes an external device, such as a server 224, and one or more computing devices 230A-230N, that are coupled to the IMD 16 and programmer 24 shown in FIG. 5 via a network 222. In this example, IMD 16 may use its telemetry module 88 to communicate with programmer 24 via a first wireless connection, and to communication with an access point 220 via a second wireless connection. In the example of FIG. 6, access point 220, programmer 24, server 224, and computing devices 230A-230N are interconnected, and able to communicate with each other, through network 222. In some cases, one or more of access point 220, programmer 24, server 224, and computing devices 230A-230N may be coupled to network 222 through one or more wireless connections. IMD 16, programmer 24, server 224, and computing devices 230A-230N may each comprise one or more processors, such as one or more microprocessors, DSPs, ASICs, FPGAs, programmable logic circuitry, or the like, that may perform various functions and operations, such as those described herein.

Access point 220 may comprise a device that connects to network 222 via any of a variety of connections, such as telephone dial-up, digital subscriber line (DSL), or cable modem connections. In other examples, access point 220 may be coupled to network 222 through different forms of connections, including wired or wireless connections. In some examples, access point 220 may be co-located with patient 14 and may comprise one or more programming units and/or computing devices (e.g., one or more monitoring units) that may perform various functions and operations described herein. For example, access point 220 may include a home-monitoring unit that is co-located with patient 14 and that may monitor the activity of IMD 16.

In some cases, server 224 may be configured to provide a secure storage site for data that has been collected from IMD 16 and/or programmer 24. Network 222 may comprise a local area network, wide area network, or global network, such as the Internet. In some cases, programmer 24 or server 224 may assemble data in web pages or other documents for viewing by trained professionals, such as clinicians, via viewing terminals associated with computing devices 230A-230N. The illustrated system of FIG. 6 may be implemented, in some aspects, with general network technology and functionality similar to that provided by the Medtronic CareLink® Network developed by Medtronic, Inc., of Minneapolis, Minn.

In some examples, processor 228 of server 224 may be configured to receive voltages or currents measured by IMD 16 to calculate impedance measurements, or may receive impedance measurements from IMD 16 via input/output device 226. Processor 228 may receive time intervals for determining LVP-RVS conduction times for determining capture thresholds of multiple pacing vectors. Processor 228 may then compute expected battery longevity and relative energy expenditure using the impedance measurements and capture thresholds for multiple selectable pacing vectors and/or other settings of IMD 16 and provide a clinician with remote viewing and analysis of energy usage of IMD 16 via input/output device 226 for facilitating programmable parameter selection and remote programming of IMD 16.

Figure 7:
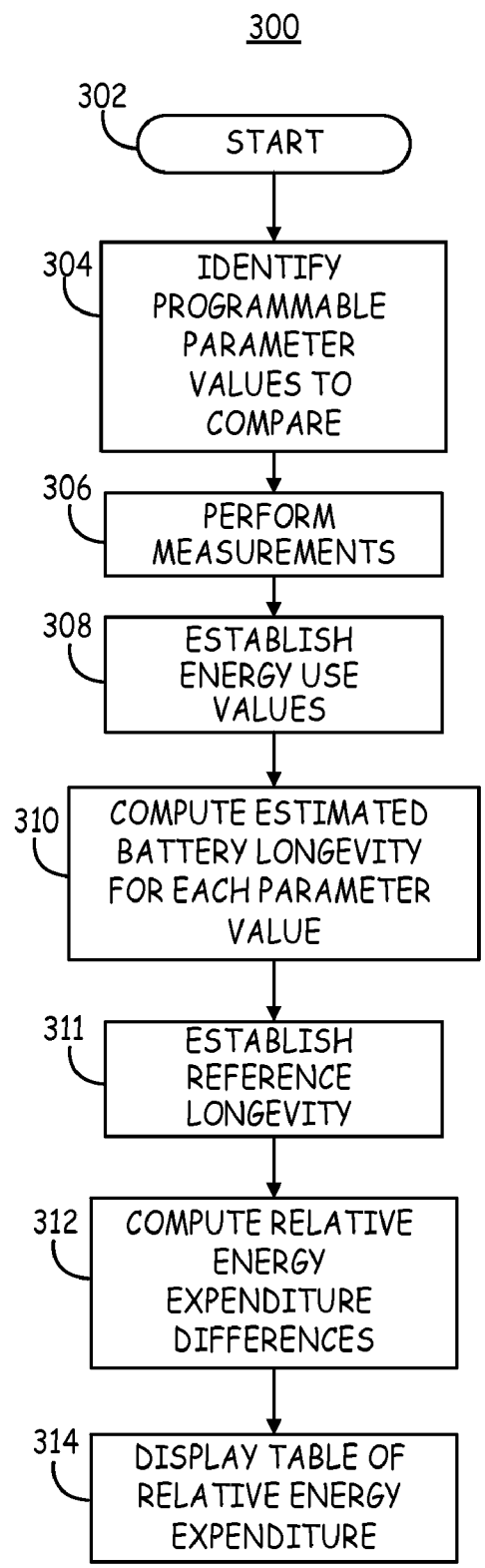
FIG. 7 is a flow chart of a method for determining relative energy expenditure for programmable IMD parameters according to one embodiment.

FIG. 7 is a flow chart 300 of a method for determining relative energy expenditure for programmable IMD parameters. In the flow charts presented herein, it is recognized that all blocks representing functional operations or decisions may not be performed in some embodiments or may be performed in a different order than the order shown.

Flow chart 300 and other flow charts presented herein are intended to illustrate the functional operation of the device, and should not be construed as reflective of a specific form of software or hardware necessary to practice the methods described. It is believed that the particular form of software will be determined primarily by the particular system architecture employed in the device and by the particular detection and therapy delivery methodologies employed by the device. Providing software to accomplish the described functionality in the context of any modern medical device system, given the disclosure herein, is within the abilities of one of skill in the art.

Methods described in conjunction with flow charts presented herein may be implemented in a computer-readable medium that includes instructions for causing a programmable processor to carry out the methods described. A "computer-readable medium" includes but is not limited to any volatile or non-volatile media, such as a RAM, ROM, CD-ROM, NVRAM, EEPROM, flash memory, and the like. The instructions may be implemented as one or more software modules, which may be executed by themselves or in combination with other software.

At block 302, a process is initiated automatically or upon user command (via programmer 24 and user interface 114 shown in FIG. 5) to generate data relating to energy expenditure. The process may be initiated automatically by the IMD processor according to periodic or programmed intervals of time. Additionally or alternatively, the process may be initiated automatically upon performing other IMD functions. For example, if a capture threshold test is initiated, the process for computing relative energy expenditure may be automatically performed as a background operation during or at the end of the capture threshold testing such that the relative energy expenditure data is automatically transmitted to and displayed on an external device or is stored for availability upon user request by way of an interrogation command. Capture threshold tests may be performed in response to detecting LOC or on a scheduled basis or on request by a user.

The process may be initiated automatically at block 302 when a lead impedance measurement is being performed. A lead impedance measurement may be performed on a scheduled or requested basis or in response to detecting LOC or suspected oversensing, in various examples.

The method for determining relative energy expenditure information may be initiated automatically upon detecting or measuring other types of events. For example, the method may be initiated at block 302 if a change in capture threshold or a change in lead impedance is detected, particularly if a programmed pacing vector is found to be associated with an increased pacing threshold or decreased lead impedance. Other triggering events which may cause the IMD processor to initiate the energy expenditure analysis may include detecting a higher than expected battery depletion or detecting a higher than expected frequency of therapy delivery.

At block 304, one or more programmable parameters and at least two associated values for each programmable parameter are identified for comparison. In various embodiments, a clinician may be selecting a pacing vector as well as selecting between different therapy delivery options, different detection algorithms, different physiological signal monitoring options, or other device features that may be selectively enabled or disabled. A clinician may establish a programmable parameter and at least two values for the parameter for which a comparative energy expenditure analysis is desired or may identify groups of programmable settings to compare at block 304 by providing user input. In other embodiments, a default set of one or more programmable parameters and associated settings, such as a standard set of available pacing vectors, is established in the memory of IMD 16 and compared automatically without requiring user input to identify programming options.

If electrical measurements are required to compute relative energy expenditure for the selected parameter values being compared, those measurements are performed at block 306. As mentioned previously, when the energy expenditure for multiple pacing vectors is being compared, capture threshold measurements are performed, e.g., according to the methods disclosed in the foregoing in conjunction with FIGS. 4A-4C, or using any capture threshold measurement algorithm implemented in the IMD. Additionally lead impedance measurements are performed.

In some embodiments, if the IMD has already been implanted for a period of time, measurements at block 306 may include identifying battery capacity already used, history of pacing demand or frequency, frequency of performing other diagnostic or event discrimination algorithms, or other historical data that may be useful in projecting an estimated battery life. A determination of battery usage may be performed according to a method as generally disclosed in U.S. Pat. No. 6,820,019 (Kelly, et al.), hereby incorporated herein by reference in its entirety. In another example, a determination of battery output impedance and/or battery output voltage may determined as generally disclosed in U.S. Pat. No. 6,016,448 (Busacker, et al.), hereby incorporated herein by reference in its entirety.

Additionally or alternatively to performing energy-related measurements at block 306, energy usage estimates may be established for various programmable IMD features or settings and stored in IMD memory as indicated at block 308. For example, if optional IMD features are implemented and can be programmably enabled or disabled, a set energy usage estimate for the given feature may be established for use in computing projected battery longevity so that relative energy expenditure with the feature enabled or disabled can be determined. Such optional features for which energy usage estimates are established may include the use of continuous capture management, arrhythmia discrimination algorithms, physiological sensing algorithms, or other optional features included in IMD 16.

At block 310, the estimated battery longevity is calculated for the parameter values (or sets of programmable settings) being compared. Various methods that may be implemented in the estimated battery longevity calculation at block 310 are generally disclosed in U.S. Pat. No. 6,901,293, (Rogers, et al.), hereby incorporated herein by reference in its entirety.

A reference longevity value is established at block 311. The reference longevity may be a maximum, minimum, or median estimated longevity computed for the parameter values, the longevity computed for a default or nominal value of the programmable parameter being evaluated, e.g. a default pacing vector and pacing voltage, or a fixed longevity value stored in associated device memory at a time of device manufacture. A fixed longevity value may be, for example, a warranty period of the programmable medical device, such as four years. Accordingly, the reference longevity value may be established by the processor computing the estimated longevities as a maximum, minimum, median or other computed longevity estimate. Alternatively, the reference longevity value is established by the processor as the longevity computed for a default or nominal programmable parameter value that is set in the device at a time of device manufacture. In other embodiments, the reference longevity value is established as a fixed value stored in memory of the medical device, such as the warranty period of the device.

At block 312, differences between the battery longevity estimates for the parameter values being compared are computed. The actual or relative differences in battery longevity estimates may be expressed in units of time such as days, weeks, months or years (or combination of thereof) or a percentage of an established reference longevity value.

At block 314 a table or graphical display of the relative energy expenditure results is generated and displayed for review by a user. Examples of a graphical user interface (GUI) including a table of relative and actual battery longevity information are given below in respective FIGS. 11 and 12.

Figure 8:
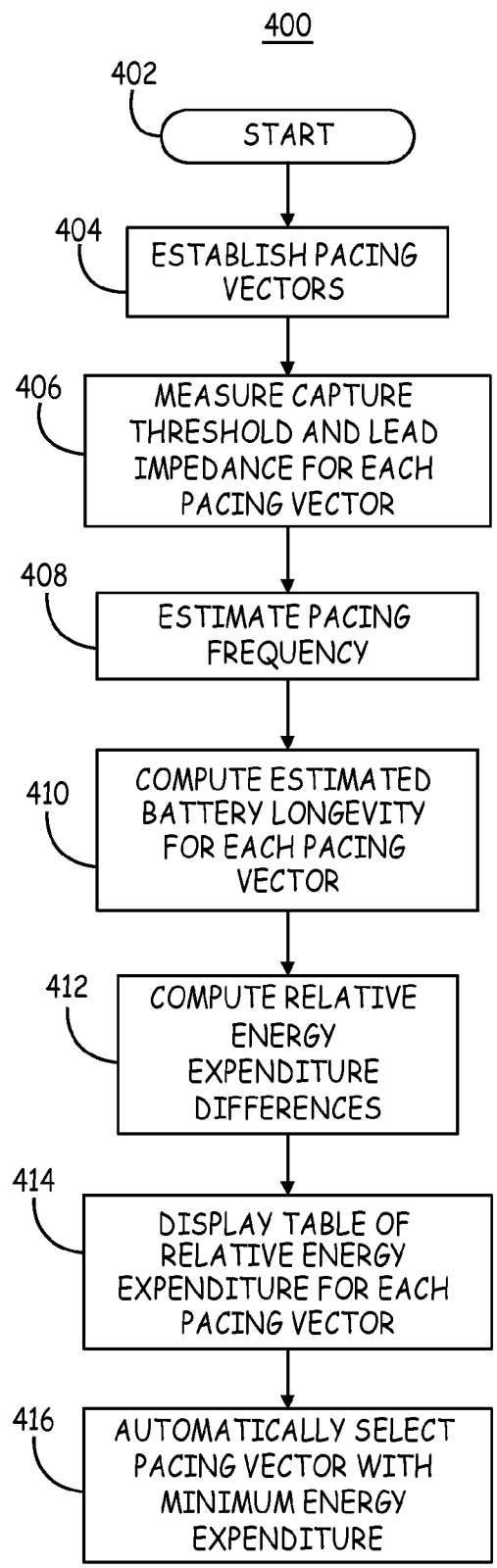
FIG. 8 is a flow chart of an illustrative embodiment for determining relative energy expenditure for multiple pacing vectors according to one illustrative embodiment

FIG. 8 is a flow chart 400 of an illustrative embodiment for determining relative energy expenditure for multiple pacing vectors. The process is initiated at block 402. The process may be initiated in any of the manners described above. At block 404, the pacing vectors to be compared are identified. A default set of pacing vectors may be established and stored in IMD memory. In some embodiments, a user may be able to select which pacing vectors are compared using a programmer user interface. The pacing vectors established for comparative energy expenditure analysis are referred to herein as "candidate pacing vectors".

At block 406, the capture threshold and an associated lead impedance is measured for each candidate pacing vector. With reference to the embodiments shown in FIGS. 2 and 3, the sixteen possible LV pacing vectors using the quadripolar lead 20 may be established as a default set of pacing vectors for which a comparative analysis is performed. Twelve bipolar combinations of electrodes 44A through 44D are available, and four unipolar combinations of each one of 44A through 44D selected in a unipolar combination with one of, for example, RV coil 62, SVC coil 66, housing electrode 58 or RV ring electrode 40 are available. The capture threshold of each of these 16 possible pacing vectors along with associated lead impedance measurements for each vector are measured at block 406.

Measuring the pacing threshold may include measuring a threshold pulse amplitude for a fixed pulse width, measuring a threshold pulse width for a fixed pulsed amplitude, or both. When both amplitude and width thresholds are determined, a strength-duration curve may be computed, for example using the Lapicque equation. The most efficient pulse width may then be derived from the strength-duration curve and this pulse width may be highlighted or displayed with relative energy expenditure data, or selected automatically by the IMD for pacing pulse delivery.

In some embodiments, a pacing frequency is either estimated or provided through user input at block 408. An estimated pacing frequency may be 100% pacing at a programmed lower rate, particularly in the case of CRT or pacing dependent therapies such as bradycardia. In other embodiments, a history of pacing frequency and pacing rates, e.g. in the case of rate responsive pacing, may be used to automatically compute an estimated pacing frequency at block 408.

At block 410, the estimated battery longevity is computed for each pacing vector under evaluation using the individual capture threshold and lead impedance measurements for the respective pacing vector. The same estimated pacing frequency is used for all pacing vectors in estimating the projected battery life.

The differences between the estimated battery longevity computations and an established reference longevity are computed at block 412. For example, a pacing vector resulting in the longest or shortest battery longevity (or other reference longevity as described above) is used as a reference value for computing relative energy expenditures of other pacing vectors. The pacing vector (or vectors) having the longest estimated battery longevity may be designated as a maximum expected battery life and all other pacing vectors may be designated with a relative time difference less than the maximum battery longevity, e.g. x number of weeks, months, or years less than the maximum expected battery longevity.

A table or graphical display of the relative estimated battery longevity is generated and displayed at block 414. The table or graphical display lists or displays each pacing vector and its associated difference in estimated battery longevity relative to a reference battery longevity (or labeled, e.g. as the maximum projected longevity, minimum or otherwise). For example, the relative estimated battery longevity may be displayed in a table, a line graph, bar graph, pie chart, time line, calendar or other display which clearly indicates the differences in the estimated battery longevities for the multiple pacing vectors.

Additionally or alternatively to generating the results displayed at block 414, the IMD may automatically select a pacing vector identified as having a minimum energy expenditure at block 416. In some embodiments, method 400 or other methods for generating relative expenditure information described herein, is initiated automatically on a periodic basis without user intervention. In this case, the IMD may be enabled to automatically select the pacing vector associated with minimum energy expenditure, or a minimum energy expenditure corresponding to a selection having acceptable physiological benefit.

Figure 9:
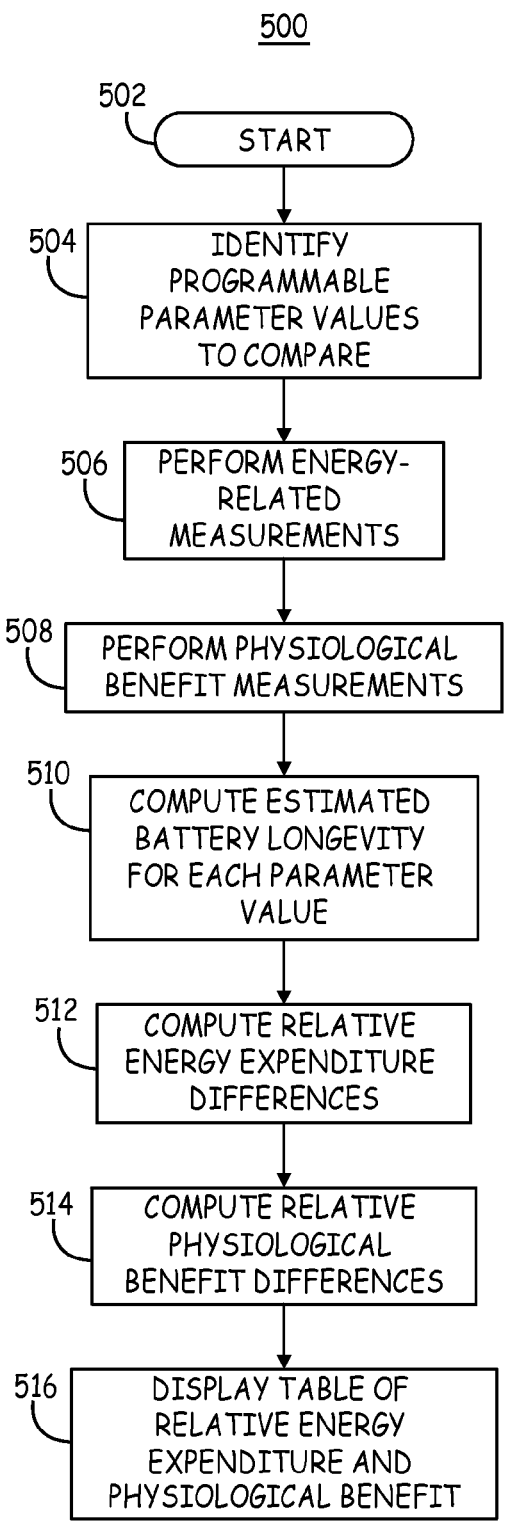
FIG. 9 is a flow chart of a method for generating a display of relative energy expenditure including a relative physiological benefit according to an alternative embodiment.

FIG. 9 is a flow chart 500 of a method for generating a display of relative energy expenditure including a relative physiological benefit. The method is initiated at block 502, either automatically, e.g. in conjunction with a capture threshold test, lead impedance test, or any of the manners described previously, or upon user command. At block 504, the programmable parameter values to be compared are identified as described previously. The parameters and associated values may be identified automatically based on a determined need for therapy or established as default parameters to be compared. For example, in the case of CRT, the parameters may automatically include all possible LV pacing vectors when a multi-polar lead is provided for LV pacing.

At block 506, energy related measurements are performed as needed for measuring the energy demand and load of a particular pacing configuration. In one embodiment, capture thresholds are measured for each possible bipolar and unipolar LV pacing electrode combination. In conjunction with the capture threshold measurements, lead impedance measurements are measured for each of the candidate pacing vectors. In this way, a capture threshold and associated electrical impedance is measured for each possible LV pacing electrode vector combination, unipolar and/or bipolar.

At block 508, a measurement correlated to a real or expected physiological benefit of supra-threshold pacing is measured. For example, a hemodynamic measurement may be measured for each of the LV pacing electrode combinations. To assess a hemodynamic response to different LV pacing electrode combinations, measurements of cardiac output or a clinical variable correlated to cardiac output or to ejection fraction may be measured, including, for example, blood pressure, cardiac wall motion, blood flow rate, heart sounds or the like. Among other possible measurements relating to physiological benefit that may be obtained at block 308 are conduction time measurements, blood oxygen saturation, and tissue perfusion.

At block 510, an estimated battery longevity is computed for each parameter value being compared (or sets of parameter values). The estimated battery longevity is computed using a predicted therapy delivery frequency, which may be based on therapy delivery history stored by the IMD or a predicted estimation made by a clinician and entered manually. The same therapy delivery frequency is used for calculating comparable battery longevity estimations for each of the identified parameters.

For example, in CRT, continuous pacing at a programmed lower rate may be assumed for all possible LV pacing electrode combinations. In other cases, the therapy delivery frequency may also be based on programmable parameters included in those identified for energy expenditure comparison. For example, different lower rates, different number of hours of pacing per day, different rate response control parameters, or other programmable parameters that will affect the rate and/or frequency of therapy delivery may be compared, which may be in addition to comparing different electrode combinations. A ventricular rate histogram could alternatively be used to determine the average rate and frequency of pacing used for energy expenditure computation.

At block 512, the relative energy expenditure differences are computed using an established reference energy expenditure. Differences in energy expenditure, e.g. expressed as battery longevity, may be presented in a variety of ways. In one embodiment, differences in the parameter(s) being tested that result(s) in the longest estimated battery life are labeled as the maximum battery longevity and the battery longevity of all other test parameters is determined in units of time less than the maximum, for example so many weeks, months or years less than the maximum battery longevity.

At block 514, the relative differences in measurements correlated to physiological benefit of the therapy are computed for each of the parameters (or sets of parameters) being compared. The relative differences may be presented in a variety of ways, depending in part on the physiological measurement used to assess or predict physiological benefit. The parameter(s) or parameter set(s) determined to provide maximum physiological benefit may be labeled as maximum and the physiological benefit determined for the other test parameters being compared may be expressed in units less than the maximum or a percentage of the maximum. Other reference values other than a maximum physiological benefit may be used, including but not limited to a measured minimum or median value or a clinically-established acceptable level.

At block 516, a table or graphic is generated and displayed for the clinician, presenting the relative energy expenditure (which may be expressed as the relative estimated battery longevity) and relative physiological benefit for each of the parameters identified for comparison.

Figure 10:
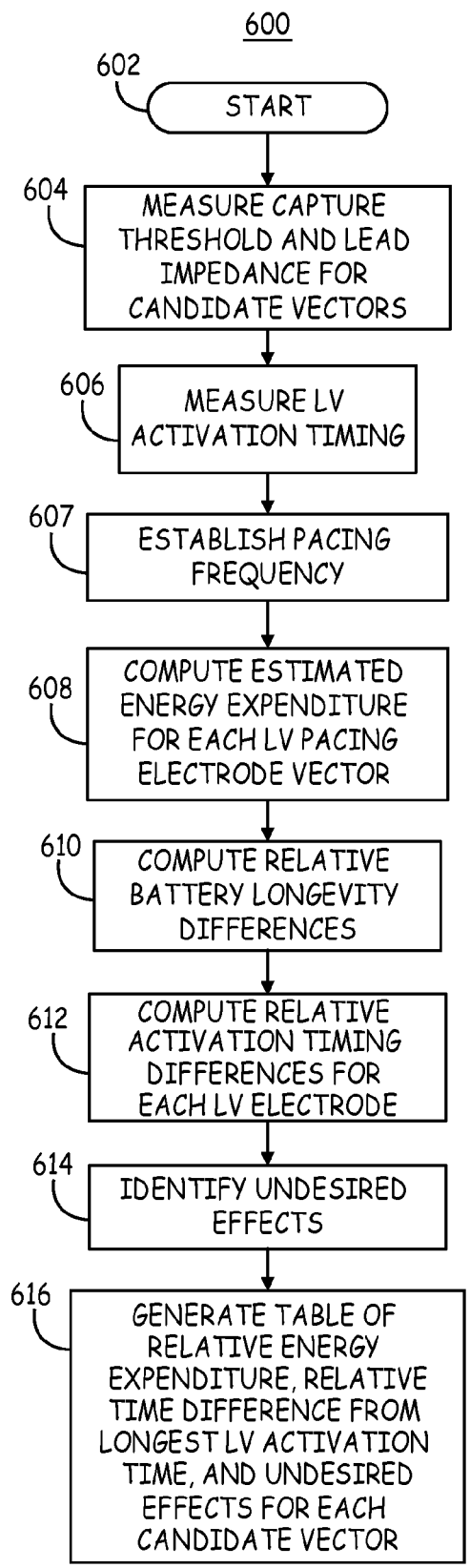
FIG. 10 is a flow chart of a method for determining and presenting relative battery longevity and physiological benefit information according to another alternative embodiment.

FIG. 10 is a flow chart 600 of a method for determining and presenting relative battery longevity and physiological benefit information according to an alternative embodiment. The method is initiated at block 602 in any of the manners described in the foregoing. At block 604, capture thresholds and associated impedances are measured for each candidate pacing vector available for pacing a selected heart chamber.

With reference to FIG. 2, each bipolar combination of electrodes 44A through 44D and a unipolar combination of each electrode 44A through 44D and an electrode positioned away from the LV, such as housing electrode 58 or RV coil electrode 62 is a candidate LV pacing electrode combination. For each of these 16 possible combinations, the capture threshold and associated lead impedance is measured. The capture threshold may be measured using various techniques. In one embodiment, the conduction time based method described in conjunction with FIG. 4 is used for measuring the LV capture thresholds for each of the twelve possible bipolar combinations and four possible unipolar combinations using the quadripolar lead 20.

At block 606, LV activation timing is measured. In CRT, the greatest therapeutic benefit may be achieved when the LV is paced at or near a location associated with the latest activation time of the ventricle. LV activation times are measured at each of the available LV electrodes relative to a reference time point, such as a sensed R-wave in the RV when no ventricular pacing is delivered. The LV activation times are measured by sensing for a LV depolarization wavefront (R-wave) at each of the LV electrodes used as sensing electrodes and coupled to electrical sensing module 82 of FIG. 3. Methods for determining LV activation times which may be adapted for use with the methods disclosed herein are generally described in U.S. Pat. No. 7,107,093 (Burnes), U.S. Publication No. 2002/0177879 (Ding, et al.), U.S. Publication No. 2004/0098056 (Ding, et al.), and U.S. Publication. No. 2004/0102812 (Yonce, et al.).

At block 607, an expected pacing frequency is established. As indicated previously, an expected pacing frequency may be based on historical pacing frequency stored by the IMD, currently programmed pacing parameters that affect pacing rate, or an estimated pacing rate and number of hours per day input by a clinician.

At block 608, an estimated energy expenditure is computed for each of the possible LV pacing vectors using the capture threshold and lead impedance data collected at block 604 for each candidate LV pacing vector individually and using the pacing frequency established at block 607 for all LV pacing vectors. The relative battery longevity differences, which may be expressed in relative units of time as compared to a maximum estimated battery longevity or other reference longevity, are computed at block 610.

Relative activation time differences are computed for each LV electrode at block 612. The electrode identified as sensing the latest activation signal is identified as having a maximum LV activation time and is generally considered to be an optimal electrode for delivering LV pacing pulses during CRT. The difference between the maximum activation time and the activation times measured for each of the other LV electrodes are determined as relative activation times and may be expressed in units of ms less than the maximum activation time, a percentage of the maximum activation time, or other relative measurement.

In addition or alternatively to determining a measurement correlated to physiological benefit, a measurement correlated to an undesired side effect may be determined at block 614. Undesired side effects of therapy delivery may occur to varying degrees with the selected parameters under comparison. During a cardiac pacing application, undesired side effects may include extraneous muscle stimulation, phrenic nerve stimulation, anodal capture, an adverse hemodynamic change, or patient-expressed symptoms.

The presence of undesired side effects may be determined automatically or entered by a user. For example, the presence of phrenic nerve stimulation or extraneous muscle stimulation may be identified using an additional physiological sensor 97 (FIG. 3) such as an EMG electrode, a motion sensor or a sensor producing a signal correlated to respiratory activity such as thoracic impedance measuring electrodes. The sensor and physiological sensing module 95 (FIG. 3) may automatically determine whether a side effect is present or absent and may determine relative differences in the intensity of the side effect when present for more than one candidate pacing vector (or other parameter being compared). Alternatively, the presence or absence may be entered by a user as each pacing electrode combination is tested.

An undesired side effect may be qualitatively measured as being present or not present. In other embodiments, a quantitative measurement of the degree or severity of an undesired side effect may be determined. For example, an adverse hemodynamic effect, such as a blood pressure change, may be measurable quantitatively.

At block 616, a table or other graphical or text display is generated for conveying both relative energy expenditure and relative activation timing differences for each candidate pacing vector. In one embodiment, the pacing vector(s) associated with the maximum estimated battery longevity are identified with each of the other pacing vectors listed with relative battery longevity expressed in a number of days, weeks, months or years less than the maximum estimated longevity. Additionally, the pacing vector(s) associated with the maximum activation times measured are identified with each of the other pacing vectors listed with relative activation time differences expressed in number of ms less than the maximum or percentage of the maximum activation time.

Provided with this information, the clinician is able to select a pacing vector based on both expected battery longevity and expected CRT benefit based on the activation timing measurements. A clinician may select a pacing vector based on a trade-off between battery longevity and expected physiological benefit. For example, a pacing vector associated with an activation time that is slightly shorter than the maximum activation time may be selected in order to achieve a longer battery longevity due to lower capture threshold and/or lead impedance. Such a trade-off may be considered to provide the greatest cost-benefit. In another example, if multiple vectors are associated with the same or similar activation times, the clinician is able to select the one that is also associated with the relatively longest estimated battery longevity or vice versa.

In addition to or alternatively to displaying the relative time difference from the longest LV activation time, the presence or absence of an undesired side effect, such as extraneous muscle or phrenic nerve stimulation, may be presented for each LV pacing vector at block 616.

Figure 11:
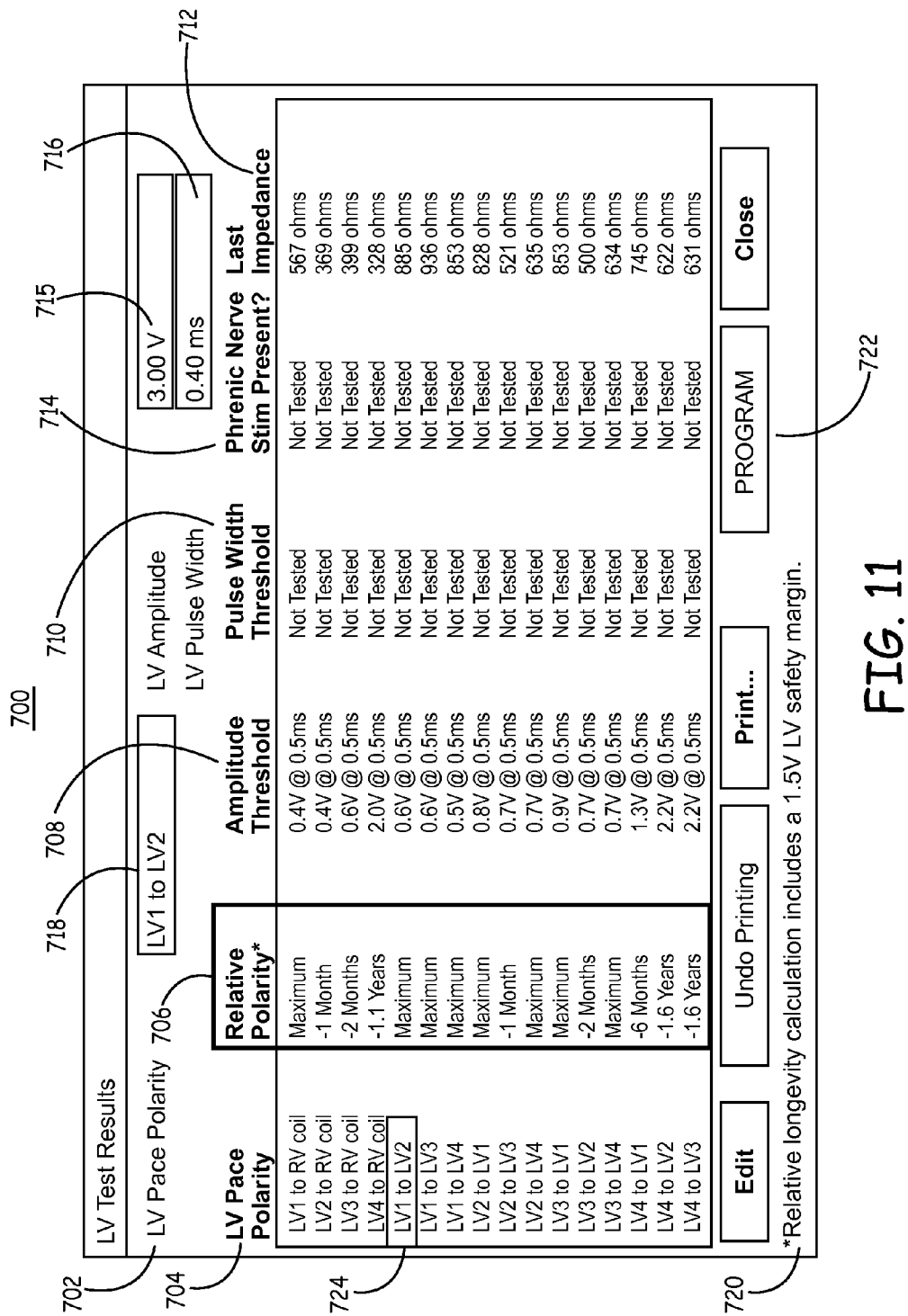
FIG. 11 is a sample graphical user interface (GUI) presented to a clinician including relative energy expenditure data generated according to one embodiment.

FIG. 11 is a sample graphical user interface (GUI) 700 presented to a clinician including energy expenditure data generated according to one embodiment. A selected test parameter field 702 displays the programmable parameter identified for comparative energy expenditure analysis. In this example, the identified parameter is LV pacing polarity. The possible selections or values for the identified parameter, i.e., LV pacing vectors, are listed in column 704. In this example, the cathode (listed first) and anode (listed second) selections for four possible unipolar LV pacing polarities and twelve possible bipolar LV pacing polarities are listed.

Relative energy expenditure for each selection of the identified parameter is listed in column 706. In this example, the relative energy expenditure is presented as estimated battery longevity differences relative to a reference maximum computed battery longevity for the given set of parameter selections. As can be seen, any selection including the LV1 electrode is associated with a maximum battery longevity. Any selection including the LV4 electrode is associated with a relatively shorter battery longevity. In other embodiments, the relative energy expenditure may be presented relative to another established reference longevity value, e.g., a minimum or median computed longevity estimate, the estimated longevity for a default parameter value, or another fixed longevity value previously established.

In at least one energy-related measurement column 708, 710 and 712, energy-usage related measurements are listed for each parameter selection, from which the relative longevity was computed, at least in part. In particular, the measured capture threshold amplitude at a fixed pacing pulse width (column 708), the pulse width threshold at a fixed pacing pulse amplitude (column 710, not measured in this example), and lead impedance (column 712) are listed for each pacing polarity selection.

If some embodiments, when both amplitude threshold and pulse width threshold are measured, the most efficient pulse width, based on strength duration-curve analysis as described previously, may be highlighted as a recommended pacing pulse width setting or automatically selected by the IMD for delivering pacing pulses at a programmed pulse amplitude.

In a side effect column 714, the presence or absence of an undesired side effect is listed. In the illustrated example, the presence or absence of phrenic nerve stimulation may be listed based on a sensed physiological signal or user input for each pacing polarity selection. Phrenic nerve stimulation has not been tested for in this example GUI.

Additionally or alternatively to side effect column 714 a physiological benefit column may be listed. For example, a column indicating relative differences between intrinsic LV activation times at each LV electrode site may be listed for the corresponding pacing polarities. An LV electrode site (LV1, LV2, LV3, or LV4) corresponding to the longest activation time would be designated as the maximum and each of the other electrode sites would be designated as a percentage or number of ms less than the maximum.

A notes field 720 is provided for conveying information pertaining to the measurements or estimated longevity. In this example, the relative longevity is indicated as being computed using the capture threshold measurement plus a default safety pacing margin.

A clinician may interact with the GUI by selecting a column heading, for example using a mouse or touch screen, to sort the data according to different column values. A clinician may review the presented information then select a parameter value to program based on the longest battery longevity, greatest physiological benefit or an acceptable trade-off between battery longevity and physiological benefit. The parameter value to be programmed may be selected in the parameter column 704. For example, a selection of LV1 to LV2 is shown highlighted at 724. A user may select the parameter value to be programmed in column 704 causing it to be highlighted, then select the program button 722.

Alternatively, a scroll down window 718 may be used for selecting the parameter value to program. Additional scroll down windows 715 and 716 may be provided for selecting pulse amplitude and pulse width. Alternatively, windows 715 and 716 may indicate the respective fixed pulse amplitude used during pulse width threshold testing or a fixed pulse width used during pulse amplitude threshold testing. In still other embodiments, the windows 715 and/or 716 may indicate default or nominal settings of the parameter being compared and for which a reference longevity value is based.

FIG. 12 shows a GUI 800 that is similar to the GUI 700 in FIG. 11 except that the estimated battery longevity column 806 lists estimated energy expenditure expressed in actual longevity values rather than relative differences. A clinician then knows the maximum estimated longevity and all other computed longevities in actual units of time rather than relative differences. It is contemplated that relative energy expenditure may be displayed in actual estimated energy usage, relative energy usage, actual estimate battery longevity, or relative estimated battery longevity differences individually or in any combination in various embodiments.

Thus, an apparatus and method for determining and presenting relative energy expenditure information associated with programmable parameters of a medical device have been presented in the foregoing description with reference to specific embodiments. It is appreciated that various modifications to the referenced embodiments may be made without departing from the scope of the disclosure as set forth in the following claims.

The invention claimed is:

1. A method, comprising:
    establishing a programmable parameter and a plurality of values of the parameter to be compared;
    enabling a module to perform a measurement for each of the plurality of values and related to energy expenditure of a battery of an implantable medical device operating according to each of the plurality of values;
    implementing a processor to compute an energy expenditure for each of the plurality of values using the measurements; and
    generating a graphical user interface displaying information corresponding to the computed energy expenditure for the plurality of values.

2. The method of claim 1, wherein establishing a programmable parameter and plurality of values of the parameter comprises storing in memory of the implantable medical device a plurality of pacing electrode vectors available for pacing a heart chamber.

3. The method of claim 2, wherein enabling a module to perform measurements comprises enabling a capture threshold measurement module to perform capture threshold measurements for each of the plurality of pacing electrode vectors and enabling an impedance measurement module to perform impedance measurements for each of the plurality of pacing electrode vectors.

4. The method of claim 3, wherein performing the capture threshold measurements comprises measuring a conduction time and comparing the conduction time to a capture detection threshold.

5. The method of claim 3, further comprising implementing the processor to compute the energy expenditure for each of the plurality of values using the capture threshold measurements, the impedance measurements, and a safety pacing margin.

6. The method of claim 2, further comprising enabling the implantable medical device to automatically select one of the plurality of pacing vectors having a minimum computed energy expenditure for pacing the heart chamber.

7. The method of claim 1, further comprising establishing a predicted frequency of therapy delivery and using the predicted frequency in computing the energy expenditures.

8. The method of claim 1, wherein generating the graphical user interface comprises computing an estimated longevity of the implantable medical device power source for each of the at least two parameter values.

9. The method of claim 8, further comprising establishing a reference longevity and displaying a difference in longevity relative to the reference longevity for each of the parameter values.

10. The method of claim 1, further comprising measuring a physiological benefit associated with each of the plurality of parameter values, determining a relative physiological benefit for each of the plurality of parameter values with respect to one of the parameter values, and displaying the relative physiological benefit corresponding to each of the plurality of parameter values in the graphical user interface.

11. The method of claim 10, wherein measuring the physiological benefit comprises measuring an intrinsic activation time at each of a plurality of pacing electrodes, and determining the relative physiological benefit for each of the plurality of values comprises determining a difference between the intrinsic activation times at each of the plurality of pacing electrodes and one of the plurality associated with a longest activation time.

12. The method of claim 1, further comprising determining whether an undesired side effect is associated with each of the plurality of parameter values and displaying in the graphical user interface information corresponding to the presence of an undesired side effect for each of the plurality of parameter values.

13. An implantable medical device system, comprising:
a programmer comprising a processor, a user interface and a telemetry module; and
an implantable medical device comprising a battery, a telemetry circuit, a module, and a processor and associated memory, the implantable medical device configured to establish a programmable parameter and a plurality of values of the parameter to be compared; enable the module to perform a measurement for each of the plurality of values and related to energy expenditure of the battery when operating according to each of the plurality of values; implement the processor to compute an energy expenditure for each of the plurality of values using the measurements; and transmit energy expenditure information to the programmer,
the programmer configured to generate a graphical user interface displaying information corresponding to the computed energy expenditure for the plurality of values.

14. The system of claim 13, wherein establishing a programmable parameter and plurality of values of the parameter comprises storing in memory of the implantable medical device a plurality of pacing electrode vectors available for pacing a heart chamber.

15. The system of claim 14, wherein enabling the module to perform measurements comprises enabling a capture threshold measurement module to perform capture threshold measurements for each of the plurality of pacing electrode vectors and enabling an impedance measurement module to perform impedance measurements for each of the plurality of pacing electrode vectors.

16. The system of claim 15, wherein performing capture threshold measurements comprises measuring a conduction time and comparing the conduction time to a capture detection threshold.

17. The system of claim 15, further comprising implementing the processor to compute the energy expenditure for each of the plurality of values using the capture threshold measurements, the impedance measurements, and a safety pacing margin.

18. The system of claim 14, wherein the implantable medical device is enabled to automatically select one of the plurality of pacing vectors having a minimum computed energy expenditure for pacing the heart chamber.

19. The system of claim 13, wherein the processor is further configured to establish a predicted frequency of therapy delivery and using the predicted frequency in computing the energy expenditures.

20. The system of claim 13, wherein generating the graphical user interface comprises computing an estimated longevity of the implantable medical device power source for each of the at least two parameter values.

21. The system of claim 20, wherein generating the graphical user interface further comprises establishing a reference longevity and displaying a difference in longevity relative to the reference longevity for each of the parameter values.

22. The system of claim 13, wherein the implantable medical device is further configured to measure a physiological benefit associated with each of the plurality of parameter values, determine a relative physiological benefit for each of the plurality of parameter values with respect to one of the parameter values,
wherein generating the graphical user interface comprises displaying the relative physiological benefit corresponding to each of the plurality of parameter values in the graphical user interface.

23. The system of claim 22, wherein measuring the physiological benefit comprises measuring an intrinsic activation time at each of a plurality of pacing electrodes, and determining the relative physiological benefit for each of the plurality of values comprises determining a difference between the intrinsic activation times at each of the plurality of pacing electrodes and one of the plurality associated with a longest activation time.

24. The system of claim 13, wherein the implantable medical device is further configured to determine whether an undesired side effect is associated with each of the plurality of parameter values and generating the graphical user interface further comprises displaying information corresponding to the presence of an undesired side effect for each of the plurality of parameter values.

25. A non-transitory computer-readable medium storing a set of instructions which when implemented in an implantable medical device system cause the system to perform a method, the method comprising:
establishing a programmable parameter and a plurality of values of the parameter to be compared;
performing a measurement for each of the plurality of values and related to energy expenditure of a battery of an implantable medical device operating according to each of the plurality of values;
computing an energy expenditure for each of the plurality of values using the measurements; and
generating a graphical user interface displaying information corresponding to the computed energy expenditure for the plurality of values.

* * * * *